United States Patent
Shimazu et al.

(10) Patent No.: US 7,264,594 B2
(45) Date of Patent: Sep. 4, 2007

(54) CARDIOVASCULAR DYNAMICS EVALUATION APPARATUS

(75) Inventors: Hideaki Shimazu, Setagaya-tu (JP); Yasuyuki Yaguchi, Okaya (JP)

(73) Assignee: Osachi Co., Ltd. (JP)

( * ) Notice: Subject to any disclaimer, the term of this patent is extended or adjusted under 35 U.S.C. 154(b) by 251 days.

(21) Appl. No.: 11/061,822

(22) Filed: Feb. 18, 2005

(65) Prior Publication Data

US 2005/0256412 A1 Nov. 17, 2005

(51) Int. Cl.
*A61B 5/02* (2006.01)
(52) U.S. Cl. .............. 600/490; 600/493; 600/494
(58) Field of Classification Search .......... None
See application file for complete search history.

(56) References Cited

U.S. PATENT DOCUMENTS

| | | | |
|---|---|---|---|
| 5,606,977 A * | 3/1997 | Ramsey et al. | 600/494 |
| 6,129,676 A * | 10/2000 | Odagiri et al. | 600/500 |
| 7,029,448 B2 * | 4/2006 | Kubo | 600/490 |

FOREIGN PATENT DOCUMENTS

| | | |
|---|---|---|
| JP | 05-038332 | 2/1993 |
| JP | 3470121 | 10/1994 |
| JP | 07-124129 | 5/1995 |
| JP | 2001-104258 | 4/2001 |

OTHER PUBLICATIONS

Information Technology Research Institute of Nagano Prefecture, Report on Research and Development Results, Nov. 7, 1994.

* cited by examiner

*Primary Examiner*—Robert L. Nasser
(74) *Attorney, Agent, or Firm*—von Simson & Chin

(57) ABSTRACT

The cardiovascular evaluation apparatus of the present invention maintains a pulse wave detection means for detecting pulse wave generated while external pressure is applied to the artery, a pulse wave pattern formulation means for formulating a pulse wave amplitude pattern that indicates the dependency characteristic of the pulse wave amplitude in regard to said external pressure, a pattern shape matching means for matching general polyangular patterns to a pattern portion of said pulse wave amplitude pattern that includes at least a part of the envelope curve where the area of the general pattern, and an index derivation means for deriving a cardiovascular dynamics index related to arterial mechanical characteristics and/or cardiac function.

22 Claims, 24 Drawing Sheets

(a)

(b)

(c)

| Type | Pattern Type | Pattern View | Typical Condition |
|---|---|---|---|
| A |  |  | Normal State |
| B |  |  | Hypertension<br>Anemia<br>Shock |
| C |  |  | Arteriosclerosis<br>Diabetes, Obesity<br>Old Age, or Intense Stress |
| D |  |  | Arrhythmia |
| E |  |  | Other Cardiac Conditions |

CARDIOVASCULAR DYNAMICS EVALUATION APPARATUS

FIELD OF THE INVENTION

The present invention relates to cardiovascular dynamics evaluation apparatus, and in particular, is concerned with measurement analysis apparatus that is suitable in the pursuit of arterial mechanical characteristics.

DESCRIPTION OF THE RELATED ART

When employing the oscillometric method to measure blood pressure, pressure is applied to the artery under an occluding cuff. The oscillometric method uses the minute oscillations generated in the internal pressure of the inflated occluding cuff to measure blood pressure. When this method is employed to measure blood pressure, an occluding cuff is affixed to the upper arm in the same fashion as with stethoscopy. After affixing the cuff, the cuff pressure is raised above systolic blood pressure. Once pressure has been raised about systolic blood pressure, pressure is then gradually decreased. In the process of decreasing cuff pressure, arterial volume varies with pulsation of blood, and minute fluctuations in pressure are produced in accordance with this arterial volume variation. The oscillometric method determines blood pressure by measuring these minute fluctuations in pressure. When cuff pressure exceeds systolic blood pressure and then gradually decreases, the amplitudes of pulse waves suddenly begin to widen. The amplitudes continue to widen until they reach their greatest magnitude near the area of mean blood pressure. The variation in pulse wave amplitudes may be explained on the basis of arterial mechanical characteristics.

In order to understand why the amplitude of pulse wave varies with the aforementioned cuff pressure, it is necessary to know the relationship of structure of the arterial walls and their mechanical characteristics. The elastic fibers and collagen fibers are the constituents of the arterial walls related to arterial extensibility. As FIG. 17 indicates, since the many tensile elastic fibers' protein fibers that are included in the arterial intima 1a and tunica media 1b are bundled in a disorderly direction, the intima 1a and tunica media 1b exhibit a small elasticity coefficient and are rich in extensibility. On the other hand, while the mechanical strength of the collagen fibers that compose the arterial adventitia 1c is higher than the elastic fibers, their elasticity is notably lower. Artery 1 may be considered as interchangeable with the constitution that comprises a spring 2 with high elastic modulus and a structure formed by combination in series of the accouplement 3 of composite fibers (that activate only when the artery expands significantly) and spring 4 of low extensibility. The spring 2 that is equal to the intima 1a and tunica media 1b and the structure that is equal to adventitia 1c formed by combination in series of the accouplement 3 and spring 4 are connected in parallel as shown in FIG. 17. In relatively low regions of active internal pressure 5 in artery 1, since accouplement 3 is in a relaxed state and the adventitia 1c is not extended, arterial wall extensibility at this point depends chiefly upon the elastic modulus of spring 2, in other words, the elasticity characteristics of the intima 1a and tunica media 1b. Thus, the extensibility of artery 1 is high, the shape of the arterial walls varies greatly with internal pressure 5, and arterial volume exhibits large-scale variation. In contrast to this, in high regions of internal pressure 5, since the intima 1a and tunica media 1b are fully expanded and the accouplement 3 is stretched out, the overall extensibility of the arterial walls is decided by the elasticity characteristics of spring 4, in other words, the characteristics of the adventitia 1c. Thus, the amount of variation in shape of the arterial walls and arterial volume becomes small.

As shown above, the properties of a normal/healthy artery manifest as the combined result of the properties of the arterial intima 1a, tunica media 1b, and adventitia 1c. Since extensibility of the intima 1a and tunica media 1b, and extensibility of the adventitia 1c are widely different, the extensibility of artery 1 varies with internal pressure 5. FIG. 18 provides a diagram of the arterial pressure-volume characteristic where the vertical axis and horizontal axis indicate the inner pressure and the arterial volume of artery 1, respectively. The figure reveals the arterial pressure-volume characteristic as exhibiting a strong non-linearity and does not indicate a proportional relationship between volume variation and internal pressure 5. Thus, even in the case that pulse pressure is equal, if the external pressure applied to the artery differs, the size of the volume variation corresponding with that pressure in regard to the pulse pressure will also be different.

Thus, as FIG. 19 indicates, even if cardiac function is constant, the observed pulse wave amplitudes will vary notably with the non-linearity of the mechanical characteristics of the artery. FIG. 19 serves to explain the relationship of the transmural pressure (difference between internal and outer pressure) of the artery and arterial volume. Here, as FIG. 20 indicates, in the case that pressure is applied to the surface of the body by a cuff, since external pressure is added to the artery through body tissue, the transmural pressure of the artery may be determined as the difference between the cuff pressure and blood pressure. Thus, as cuff pressure gradually decreases, the intensity of observed pulse waves also varies with time, as indicated in FIG. 21, resulting in the type of pulse wave amplitude pattern indicated in FIG. 22.

Previous technology employed the fact that the mechanical characteristics of the artery and cardiac function could be conjectured from the pulse wave amplitude pattern above to analyze the relationship of the pulse wave amplitude pattern (manifest during blood pressure measurement with the oscillometric method) and circulatory dynamics, and classified the result into 5 types of Fundamental Patterns A through E as indicated in FIG. 23. Here, FIG. 24 indicates an artery with normal/healthy characteristics classifiable as Fundamental Pattern A, FIGS. 25 and 26 indicate the characteristics of a sclerotic artery classifiable as Fundamental Pattern C, and FIG. 27 indicates the characteristics of an arrhythmic artery classifiable as Fundamental Pattern D, and FIG. 28 indicates the characteristics of an artery with cardiac disease.

In addition, apparatus and methods have been proposed for analyzing arterial stiffness that employ the fact that the aforementioned pressure-volume characteristic and degree of arteriosclerosis indicate high correlation (as may be seen in FIGS. 25 and 26); in other words, each type of technique that pursues an index of arterial stiffness based on changes in the shape of the pulse wave.

As explained above, in order to obtain the pulse wave amplitude pattern, it is necessary to detect the components of the overlapping pulse waves that are manifest in cuff pressure when the pressure from an occluding cuff on a living organism's body surface that has been inflated to apply pressure to the body surface is gradually released. However, at the time the components of the pulse waves are detected, there are cases when arch factor and fluctuation of breathing during blood pressure measurement make it difficult to obtain a precise pulse wave amplitude pattern corresponding with the mechanical characteristics of the artery and cardiac function. In particular, when data analysis is performed automatically by computerized apparatus, since a method for eliminating the noise component included in the pulse wave amplitude series have yet to be established, there is a problem in that an objective determination cannot be made.

In addition, since it is unclear as to what extent the arterial pressure-volume characteristic can be estimated from the shape of the pulse wave amplitude pattern, and furthermore, since there is no clear standard regarding the portion of the shape of the pulse wave amplitude pattern to be employed for extracting a cardiovascular dynamics index, in the case that analysis is conducted by computer, mistaken assessments can result and the accuracy of the index that indicates the degree of arterial stiffness can suffer a decline depending upon the shape of the obtained pattern shape.

SUMMARY OF THE INVENTION

Here, the object of the present invention is to offer apparatus that reduces the effect of noise components in determining the pulse wave amplitude pattern. Another object is to offer an apparatus that increase the accuracy of the obtainable cardiovascular dynamics index.

Taking into account the situation described above, the cardiovascular dynamics evaluation apparatus of the present invention provides: a pulse wave detection means for detecting pulse waves when external pressure is applied to the artery, a pulse wave amplitude pattern formulation means for formulating a pulse wave amplitude pattern that indicates the dependency characteristic of the pulse wave amplitude in regard to said external pressure from the value detected by said pulse wave detection means, a pattern shape matching means for matching general polyangular patterns to a pattern portion of said pulse wave amplitude pattern that includes at least a part of the envelope curve where the area of the general polyangular pattern, an index derivation means for deriving a cardiovascular dynamics index related to arterial mechanical characteristics and/or cardiac function based on said general pattern matched shape. Since the present invention matches at least one portion of the pulse wave amplitude pattern that includes the envelope curve of the pulse wave amplitudes with a polyangular general pattern and identifies the shape of at least one portion of the pulse wave amplitude pattern according to polyangular shapes, the effect of noise can be reduced by the fact that the profile of the shape of the pulse wave amplitude pattern can be extracted as a whole within the pattern matching range. In addition, since the profile of the pulse wave amplitude pattern is expressed as polyangular general patterns, the pattern matching method is versatile, can flexibly respond to many kinds of pulse wave amplitude pattern shapes, and can derive a highly accurate cardiovascular dynamics index that possesses a high degree of accuracy in comparison with traditional methods, which derive a cardiovascular dynamics index based on points of information drawn from the pulse wave amplitudes. Furthermore, since the present invention employs a limited number of polyangular general pattern shapes, derivation of a cardiovascular dynamics index based on matching of general patterns can be conducted with ease.

Here, a cuff can be employed to apply pressure on the body surface as a means for applying external pressure to the artery, but with the present invention, any mechanism may be used as long it can apply external pressure on the artery. For example, a pressure-applying belt may be used, which can apply external pressure on the artery by constricting the circumference of the arm. In addition, the means of pulse wave detection is not limited to detection with a pressure sensor that detects cuff pressure but may consist of a pressure sensor set installed on the body surface.

Furthermore, the general patterns may be formed so that matching can be performed with either the entirety or a portion of the pulse wave amplitude pattern. The polyangular general patterns are fundamental structures of pattern shapes for matching with pulse wave amplitude patterns; for example, they may be general shapes with a determined number of angles as with triangles, quadrangles, pentagons, trapezoids, or they may consist of conditions (the angle of the area between adjacent areas, the range of the adjacent areas, or the degree of parallelism of non-adjacent areas) in addition to number of angles as is the case with a combined triangle and quadrangle. Since the general patterns are not limited for instance to perfect triangles or trapezoids but may express all of these cases, there is complete degree of freedom in the shape of their patterns.

Moreover, when pattern matching is performed on the entirety of the pulse wave amplitude pattern, a multiple number of polyangular patterns such as Fundamental Patterns A through E indicated in FIG. 23 may be employed. For example, a pentagon general pattern can be employed in the case of fundamental pattern A through C. Furthermore, when pattern matching is performed on a portion of the pulse wave amplitude pattern, an extremely simple (few angles) shape such as a triangle or trapezoid can also be employed as a general pattern.

In addition, the cardiovascular dynamics evaluation apparatus based on the present invention provides as its salient features: a pulse wave detection means for detecting pulse waves when external pressure is applied to the artery, a pulse wave amplitude pattern formulation means for formulating a pulse wave amplitude pattern that indicates the dependency characteristic of the pulse wave amplitude in regard to said external pressure from the value detected by said pulse wave detection means, a pattern shape matching means for matching general trapezoid patterns to a pattern portion including the envelope curve of said pulse wave amplitude pattern that is defined by applying a lower limit threshold to said pulse wave amplitude pattern, an index derivation means for deriving a cardiovascular dynamics index related to arterial mechanical characteristics based on said general pattern matched shape. Since the present invention matches a general pattern with the upper part of the pulse wave amplitude pattern by setting a lower limit on the pulse wave amplitude values of the pulse wave amplitude pattern, it is possible to calculate a cardiovascular dynamics index that objectively indicates the mechanical characteristics of the artery, and in particular, the elastic characteristic of the intima and tunica media, by extracting the profile of the shape revealed by the maximum pulse amplitude value or values. Furthermore, a cardiovascular dynamics index that objectively indicates the mechanical characteristics of the artery, and in particular, the elastic characteristic of the intima and tunica media, can be easily and accurately be obtained from the shape of the upper part of the matched trapezoidal pattern (hereinafter described as upper width W and width W') by using the trapezoidal general patterns.

DESCRIPTION OF THE PREFERRED EMBODIMENTS

Figure 1:
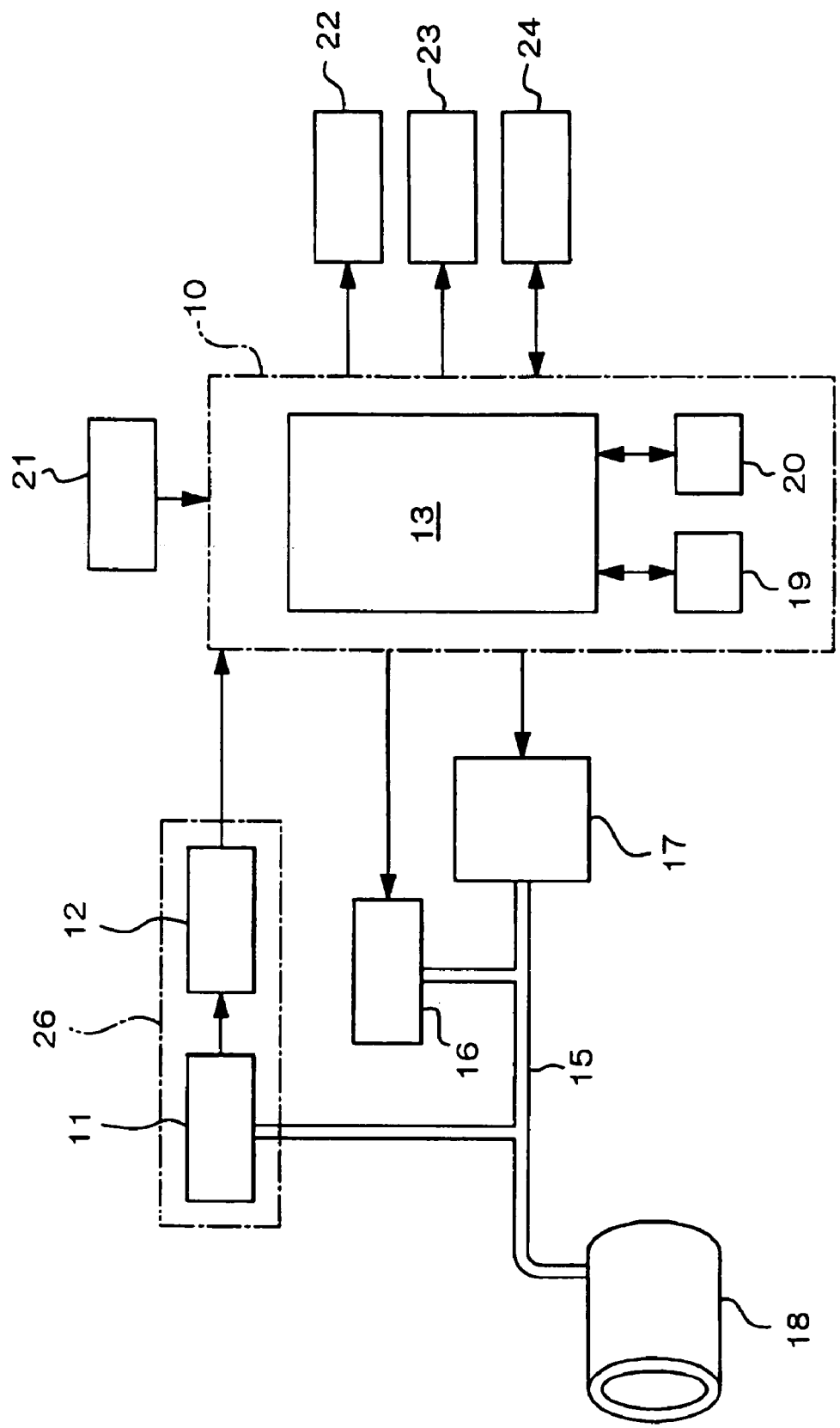
FIG. 1 schematically shows an overall block diagram of cardiovasculer evaluation apparatus in accordance with an embodiment of the present invention.

Next, the details of the embodiment of the present invention including the cardiovascular evaluation method will be explained using the attached figures. FIG. 1 is an overall block diagram of cardiovascular evaluation apparatus in accordance with an embodiment of the present invention. In this cardiovascular dynamics evaluation apparatus, a cuff (in other words an inflatable arm band) 18 for applying pressure to the artery of a living body, a pressure detection device 11 composed of a diaphragm pressure meter, a distortion sensor, and other means for detecting cuff pressure, a constant-speed release means 16 composed of a pressure reducing valve, flow controller valve, and other means for venting air in cuff 18, and a compression means 17 composed of a compression pump and other means for applying pressure inside cuff 18, are connected to each other through piping 15 consisting of flexibility tubes. Pressure detection device 11 detects the internal pressure of cuff 18 (in other words cuff pressure) and outputs detection signal cuff pressure Pc to pressure detection circuit 12. Pressure detection circuit 12 converts signals detected by pressure detection device 11 (for instance A/D analog/digital) and supplies control unit 10 consisting of the microprocessor and other means. Here, pressure detection device 11 and pressure detection circuit 12 compose pressure detection means 26 that is one part of the pulse wave detection means. The pulse wave detection means comprises cuff 18, pressure detection means 26, and part of the operating program conducted by the aftermentioned control unit 10.

Control unit 10 comprises the CPU (Central Processing Unit) 13, buffer memory 19, which contains RAM (Random Access Memory), storage memory 20, which contains ROM (Read Only Memory), and in addition when necessary, an internal bus and input-output circuit. Buffer memory 19 temporarily records the processing result of the operating program conducted by CPU 13. In addition, the aforementioned operating program and all setting values are recorded in storage memory 20. The external operating unit 21 that contains the external operation components such as an operation switches, the display apparatus 22 that visually displays the processed result, the printing apparatus 23 that records processed results on media such as paper, and input-output terminal posts 24 that output processed data and input external data are connected in control unit 10.

Furthermore, it is also possible for control unit 10 to be composed of a mere calculation circuit rather than a microprocessor (MPU). In addition, while the control system centered around control unit 10 and the detection system that includes cuff 18 form an integrated body in the present embodiment, the detection system and control system may also be maintained as separate bodies. For example, it is possible to employ detection apparatus forming the detection system and control apparatus consisting of a personal computer. In addition, the process of detection and the analysis of the detected results are performed together by the operating program in the present embodiment, but it is possible to separately maintain detection program that performs processing of detection and a program that processes analysis of detected results.

Figure 2:
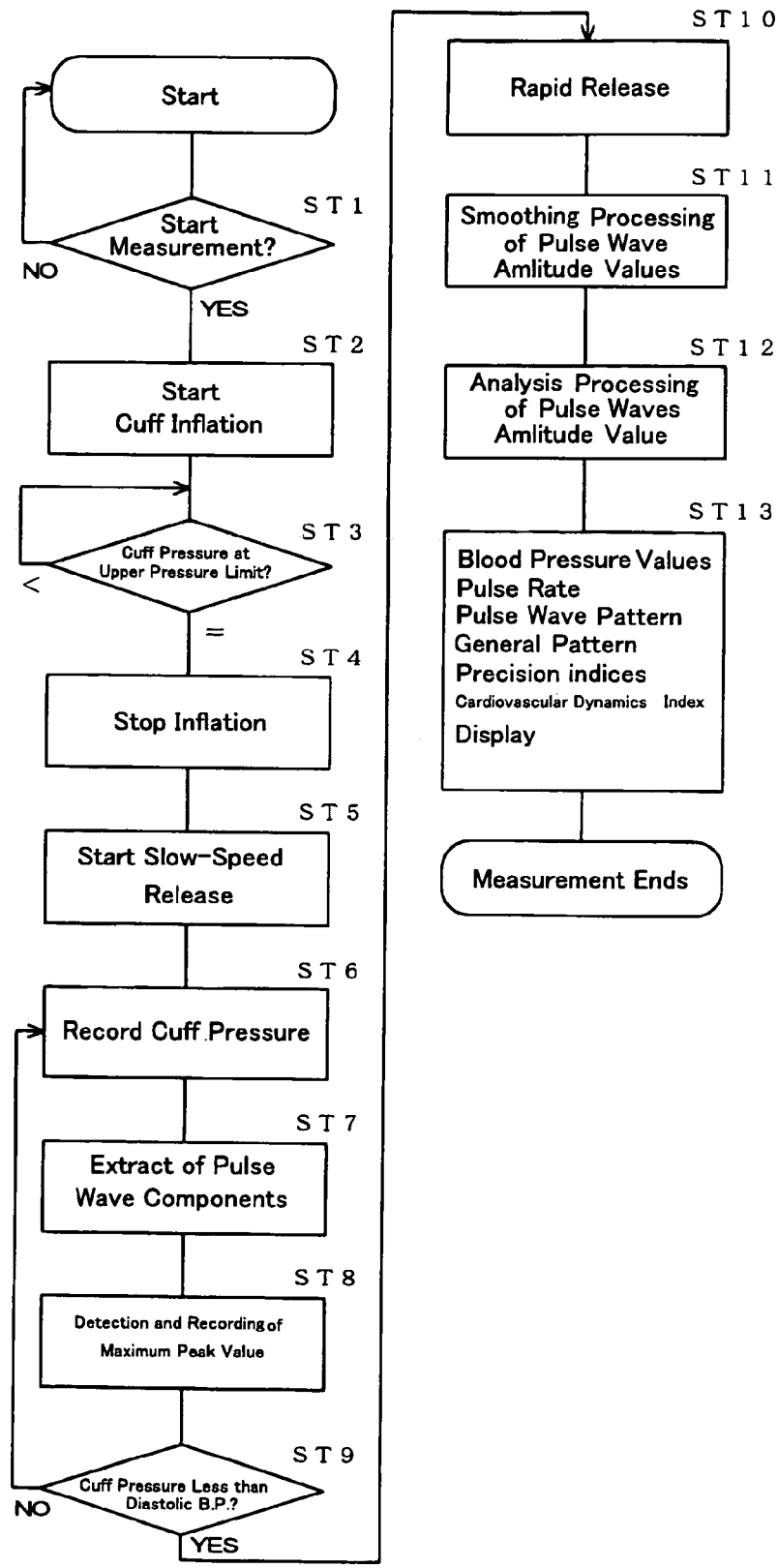
FIG. 2 schematically shows a flow chart of operational program in accordance with an embodiment of the present invention.

FIG. 2 is a flow chart of operational program in accordance with an embodiment of the present invention. When employing the cardiovascular dynamics evaluation apparatus of the present embodiment, one must first fix cuff 18 at a place on the subject where pressure may be applied to the artery. Here, the arm, ankle, or wrist may serve as places for attaching cuff 18 as long as it is possible to apply pressure to the artery and measure blood pressure. Once cuff 18 has been affixed and operation initiated in external unit 21, measurement begins (ST1), and control unit 10 supplies a driving signal to compression means 17, which inflates cuff 18 (ST2). In this inflation process, it is desirable for the constant-speed release means 16 to be closed to stop release of pressure. At this time, cuff pressure is detected by the pressure detection means 26, and when cuff pressure reaches goal pressure (ST3), control unit 10 causes inflation to complete by compression means 17 (ST4). The goal pressure should be a sufficiently higher value than the systolic blood pressure of the subject, for instance, it should be set at around 210 mmHg.

When the aforementioned inflation process completes, pressure release by the constant-speed release means 16 begins (ST5) along with continuous detection of cuff pressure by aforementioned pressure detection means 26 and recording in the buffer memory 19 of control unit 10 (ST6). In this step, the pressure detection circuit 12 performs sampling of sequential detection values from pressure detection 11 at predefined sampling cycles, for instance, sampling of sequential detection values at 50 millisecond intervals, and the cuff pressures corresponding with these detection values are stored in the buffer memory 19 of Control Unit 10.

In addition, at this time, the extraction of the components of the pulse wave is conducted (ST7) based on the detected cuff pressures, and the maximum value (peak value) of the pulse wave is detected and recorded (ST8). In concrete terms, in the control unit 10, the difference values of supplied cuff pressure data are calculated and after eliminating components corresponding with the rate of cuff deflation in the series of pressure differences, the pulse wave amplitudes are derived from only positive pressure differentials for each pulse. The maximum value of the pulse wave amplitude is then detected. The pulse wave amplitude maximum peak value is then recorded in buffer memory 19 along with the cuff pressure values and the time of their appearance. The cuff pressure decreases, and when it falls below diastolic blood pressure (ST9), cuff pressure measurement is complete and the constant-speed release means 16 opens to commence rapid release (ST10).

The aforementioned method of deriving pulse wave amplitudes calculates the differential data from detected cuff pressure data, eliminates those values corresponding with the cuff pressure decrease rate (incline) from this differentiated data, formulates pulse wave differential data, and accumulates only the positive values from this differential data. However, in the present embodiment, since it is sufficient to obtain the pattern that reflects the dependence characteristic in regard to the cuff pressures of the pulse intensities (external pressure applied to the artery), any type of value may be employed for pulse wave amplitude as long as it maintains a positive correlation with pulse wave intensity, whether it be the pulse wave peak value themselves, the pulse wave differential signals, or the differential signal peak values.

When the aforementioned measurement is complete, control unit 10 conducts smoothing process of obtained pulse wave amplitude data series (ST11). This process, by comparing previous pulse wave amplitude range, the current pulse wave amplitude range, and the next pulse wave amplitude range, makes it possible to determine whether the detected pulse wave amplitudes are normal pulse wave amplitudes. When back and fore data have been compared and the pulse wave amplitude range is judged to be abnormal, this pulse wave amplitude is eliminated and exchanged with the average value of the fore and back data and in addition, or alternatively, smoothing process of the pulse wave amplitude series is conducted by migration averaging of the pulse wave amplitude series. As a result of this process, the minute fluctuation components that cause noise are minimized as abnormal data is eliminated from the pulse wave amplitude series.

Figure 3:
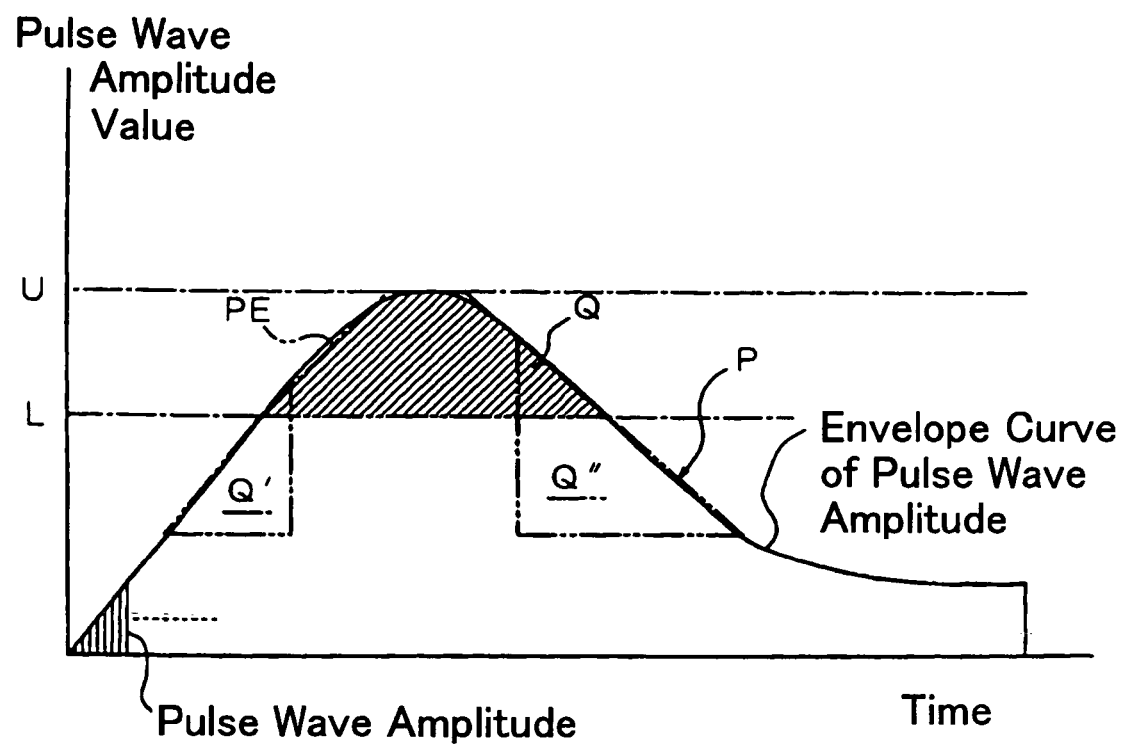
FIG. 3 shows a graph to explain correlation of pulse wave amplitude pattern and general pattern in accordance with an embodiment of the present invention.

Next, analysis process (ST12) is performed on the pulse wave amplitude values obtained from the aforementioned method. In this analysis process, the pulse wave amplitude pattern, systolic blood pressure value, mean blood pressure value, diastolic pressure value, and the pulse rate are determined. Here, as indicated in FIG. 3, the pulse wave amplitude pattern P is formulated as a pattern corresponding with the shape of the pulse wave amplitude envelope curve following interpolation and smoothing process of the pulse wave amplitude data. In all cases, the formulated pulse wave amplitude pattern indicates the dependency characteristic to the arterial pulse wave intensities, in other words, the detected arterial transmural pressure differences. In concrete terms, the pulse wave amplitude pattern appears as a graph, where the horizontal axis x is external pressure (cuff pressure), arterial transmural pressure, or in the case of the present embodiment, time, and where vertical axis y is the values of pulse wave amplitudes. In addition, the shape of the general pattern matched with pulse wave amplitude pattern, the precision index for this general pattern shape, and the cardiovascular dynamics index calculated from this general pattern shape are also derived in this analysis process according to the following methods.

Furthermore, since the aforementioned pulse wave amplitude pattern can be obtained as a the result of the pattern pulse wave detection method related to the present embodiment, rather than being limited to detection during decline in cuff pressure, a method that performs detection as cuff pressure increases, or a method that varies cuff pressure at discretion, may be employed to measure data. Any of these methods may be employed as long as the pulse wave amplitude values and the external pressure (or the transmural pressure difference in regard to the artery) when these values were obtained can be measured within a predefined range in the area of mean pressure.

Lastly, the blood pressure values, pulse rates, pulse wave amplitude patterns, shapes matched patterns, precision index values, and cardiovascular dynamics index values obtained with the aforementioned analysis process can be displayed with display apparatus 22, printed with printing apparatus 23, or output as data with input-output terminals 24 (ST13).

Figure 4:
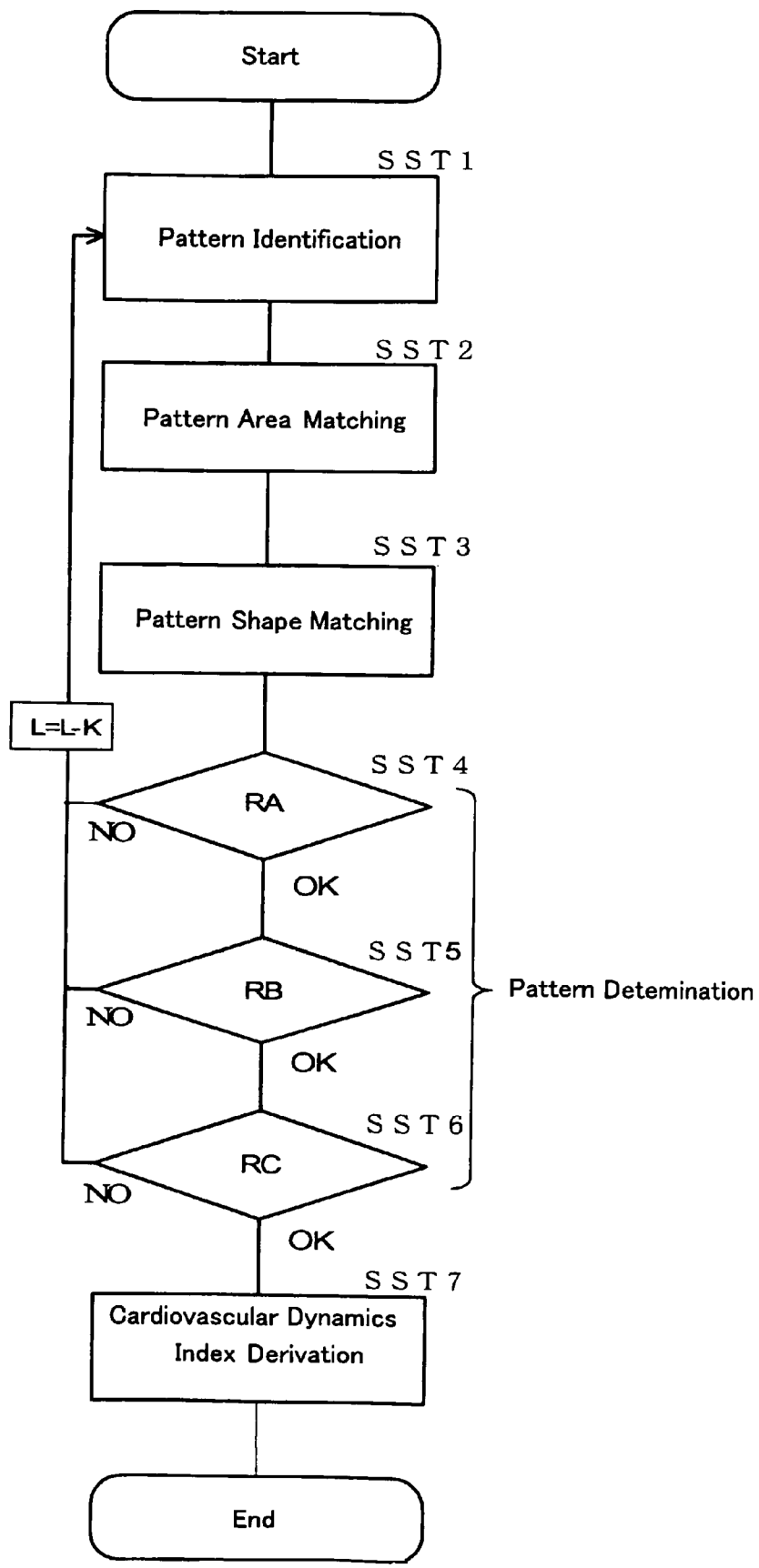
FIG. 4 schematically shows a flowchart of analysis process in accordance with an embodiment of the present invention.

An explanation is provided here of the ranges associated with the matching the general pattern shape with the pulse wave amplitude pattern, the derivation of the cardiovascular dynamics index, and the derivation of the precision index of the general pattern matching, all of which form part of the analysis process (ST12) regarding the aforementioned pulse wave amplitude values. FIG. 4 is a flowchart of analysis process in accordance with an embodiment of the present invention. These processes include the process of identifying from the pulse wave amplitude pattern the part of the pattern (pattern portion) to be employed for subsequent process (for instance, SST1 in FIG. 4), the pattern area matching process (for instance, SST2 in FIG. 4) that establishes the area of the general pattern as equal to the area of the aforementioned pattern portion (of the pulse wave amplitude pattern), the pattern shape matching process (for instance, SST3 in FIG. 4) that matches the general pattern with the aforementioned pattern portion, the pattern determination process (SST4 to SST6) that determines the matched shape, and the index derivation process (for instance SST7 in FIG. 4) that derives the cardiovascular dynamics index. Below follows an example of the execution of the series of aforementioned processes that match the pulse wave amplitude pattern peak area with a trapezoidal general pattern and on the basis of this general pattern, derive a cardiovascular dynamics index that indicates the degree of arterial stiffness.

[Pattern Identification Process (SST1)]

First, in formulated pulse wave amplitude pattern P indicated in FIG. 3, pattern portion Q, which possesses the pulse wave amplitudes exceeding lower limit L of pulse wave amplitude pattern P (in the present embodiment 84% of the maximum value of pulse wave amplitude pattern P), is extracted as the portion of the pattern that reflects the elastic characteristics of the arterial intima 1a and tunica media 1b. Here, as long as lower limit L serves to define the region that reflects the qualities of the arterial intima 1a and tunica media 1b, it can be an arbitrary value, but, in particular, 40 to 90% of the aforementioned maximum value is desirable. When lower limit L is too small, parts other than the part reflecting the elastic characteristics of the arterial intima 1a and tunica media 1b become incorporated leading to a decline in the degree to which the obtained cardiovascular dynamics index can accurately reflect the elastic characteristics of the arterial intima 1a and tunica media 1. On the other hand, when lower limit L is too large, the effect of noise and measurement error also becomes large, leading to a loss in the accuracy of the obtained cardiovascular dynamics index in reflecting the aforementioned elastic characteristics.

In addition, in the case of the present embodiment, the upper limit U of the aforementioned pattern portion Q is equal to the maximum pulse wave amplitude value in aforementioned pulse wave amplitude pattern P. However, it is acceptable to set this upper limit U as a value lower (for instance 95 to 99% of the maximum value) than the maximum pulse wave amplitude value in aforementioned pulse wave amplitude pattern P. In this way, when upper limit U is adjusted to define pattern portion Q, it is possible to reduce the effect of noise in the area of the maximum value of the pulse wave amplitudes.

Furthermore, in the present embodiment, only the pattern portion Q indicated in FIG. 3 is explained, but as long as it contains the envelope curve of the pulse wave amplitudes in the pulse wave amplitude pattern, any pattern portion is acceptable; for instance, pattern portion Q' (pulse wave amplitudes increase in value in the process of decreasing external pressure) and pattern portion Q" (pulse wave amplitudes decline in the process of decreasing external pressure) indicated by chain double-dashed lines in FIG. 3 may be employed as well as the entirety of pattern P. It is desirable to employ the after-mentioned general pattern corresponding with pattern portion Q' and pattern portion Q" as a triangle.

Figure 5:
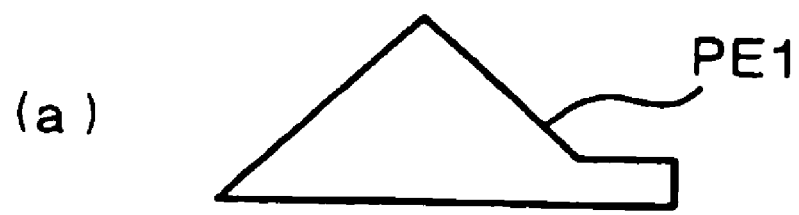
FIG. 5 shows a graph to explain model of general patterns of different shaped in accordance with an embodiment of the present invention.
Figure 5:
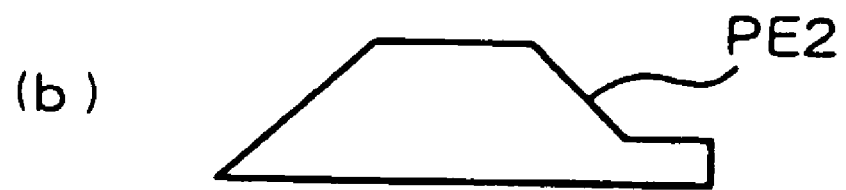
Figure 5:
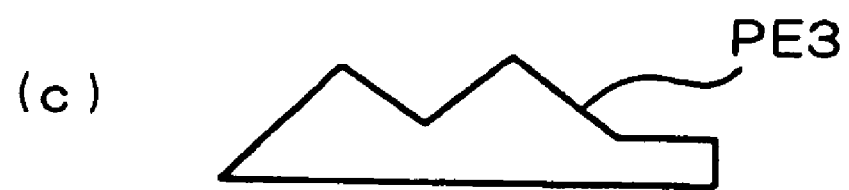
Figure 23:
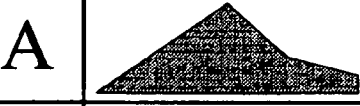
FIG. 23 shows a diagram to explain relationship of pulse wave amplitude pattern fundamental pattern and various cardiovascular conditions.
Figure 23:
Figure 23:
Figure 23:
Figure 23:
Figure 23:
Figure 23:
Figure 23:
Figure 23:
Figure 23:
Figure 24:
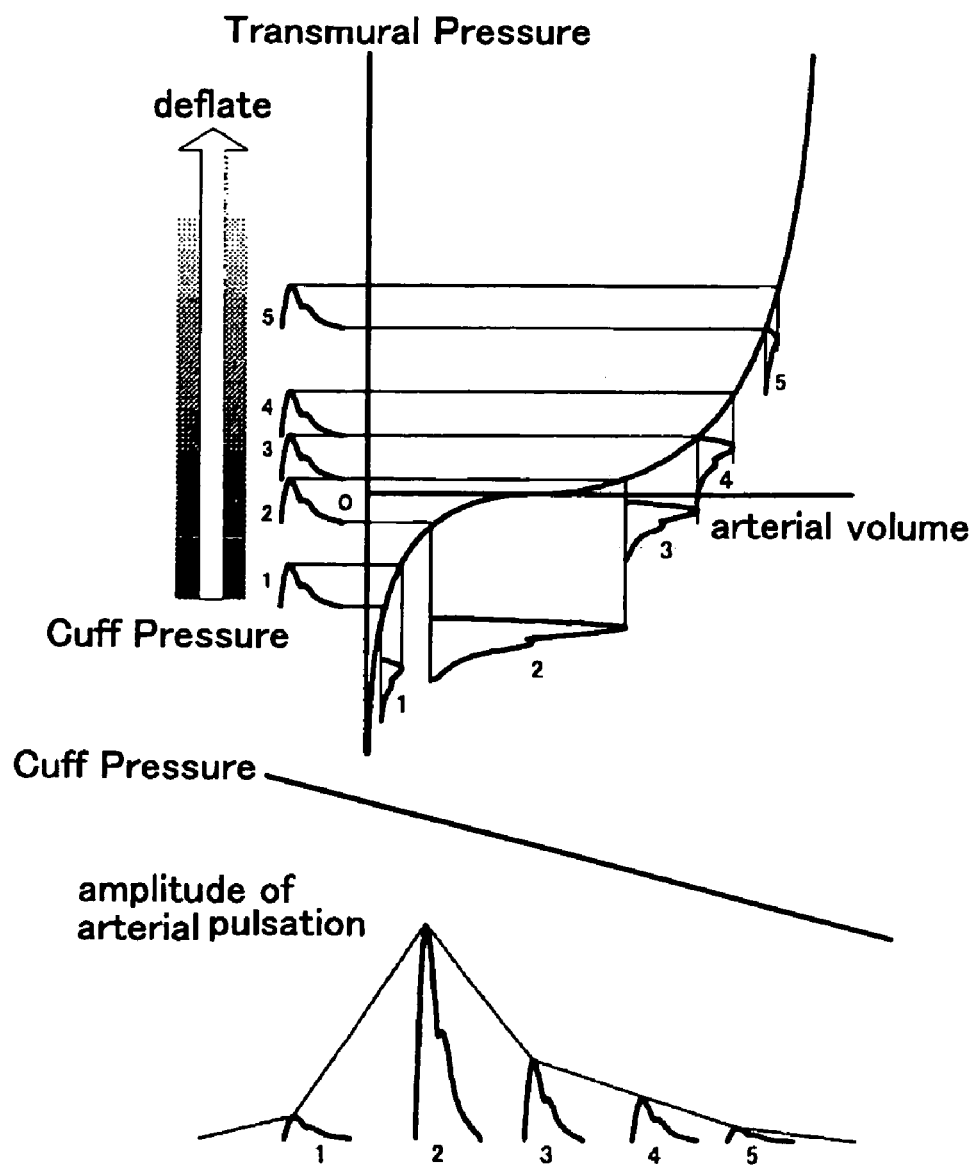
FIG. 24 shows a graph to explain relationship of fundamental pattern A and arterial elastic characteristic.
Figure 25:
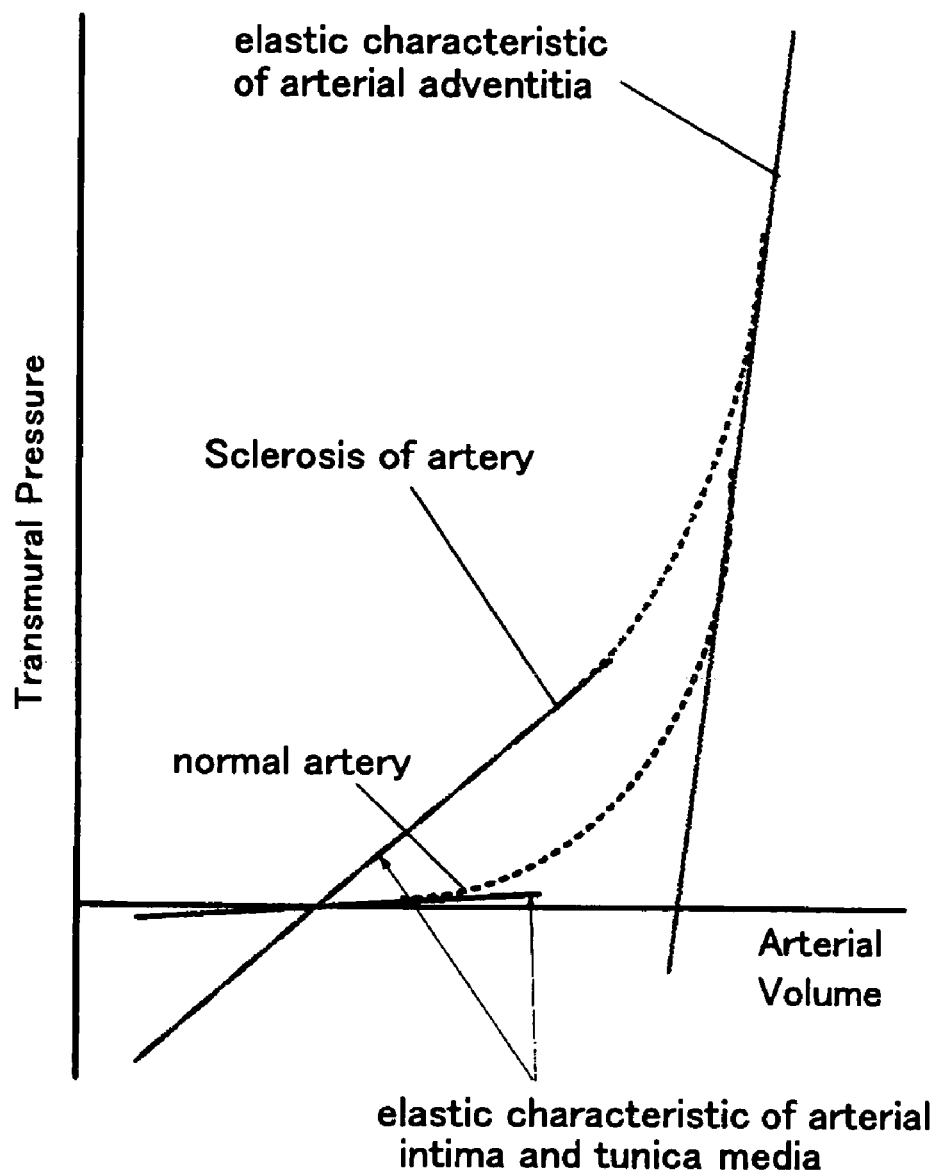
FIG. 25 shows a graph to explain variation depending on degree of stiffness of arterial elastic characteristic.
Figure 26:
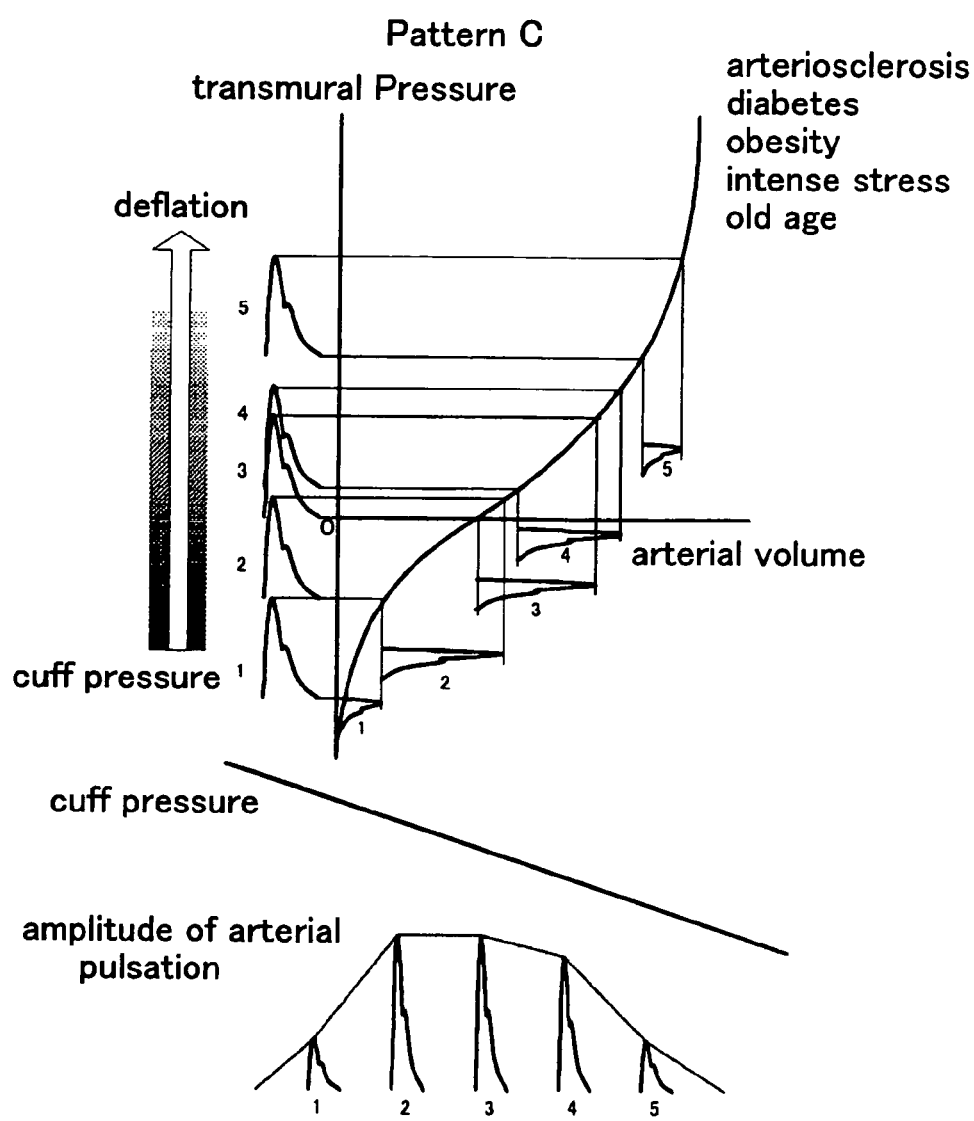
FIG. 26 shows a graph to explain relationship of fundamental pattern C and arterial elastic characteristic.
Figure 27:
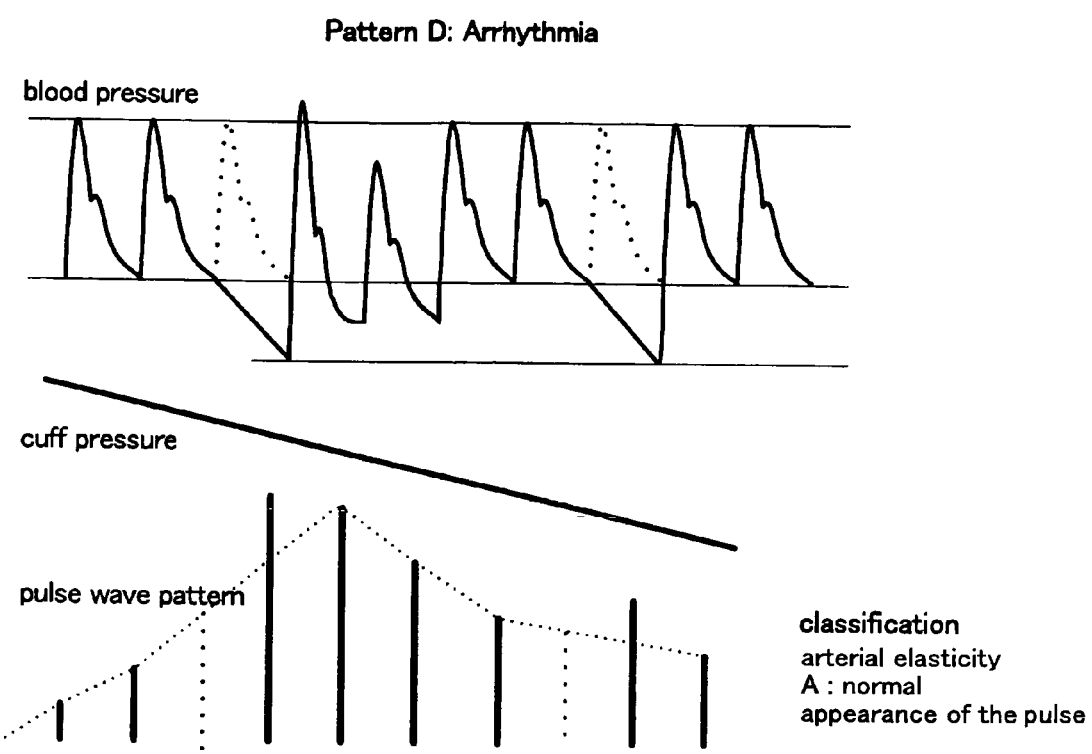
FIG. 27 shows a graph to explain fundamental pattern D.
Figure 28:
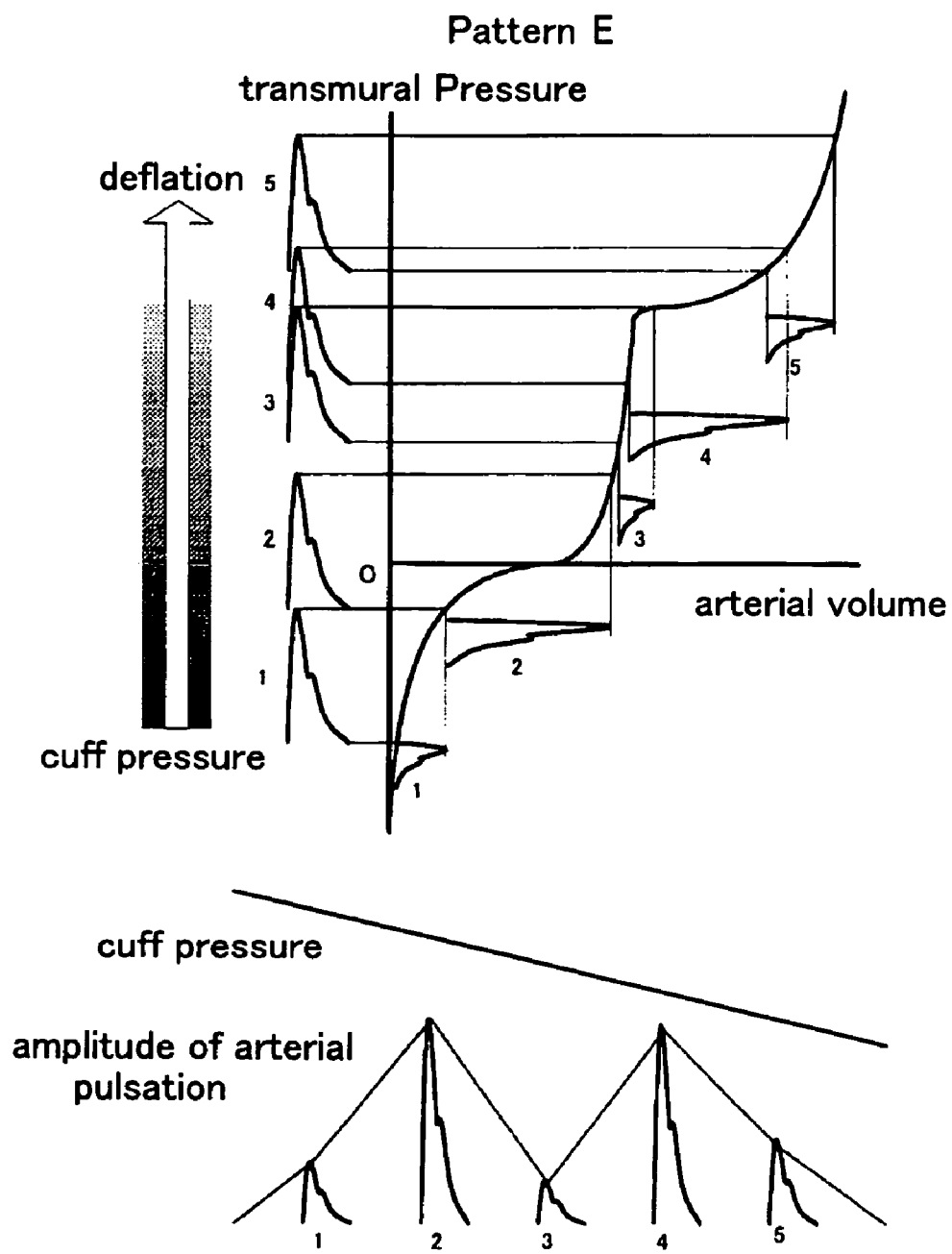
FIG. 28 shows a graph to explain relationship of fundamental pattern E and arterial elastic characteristic.

Moreover, in the case that the entirety of pattern P is to serve as the subject of matching, it is desirable to employ a general pattern corresponding with one of Fundamental Patterns A through E indicated in FIG. 23; for instance, it is desirable to employ the pentagons or hexagon general patterns PE 1 through PE3 indicated in FIG. 5.

Figure 6:
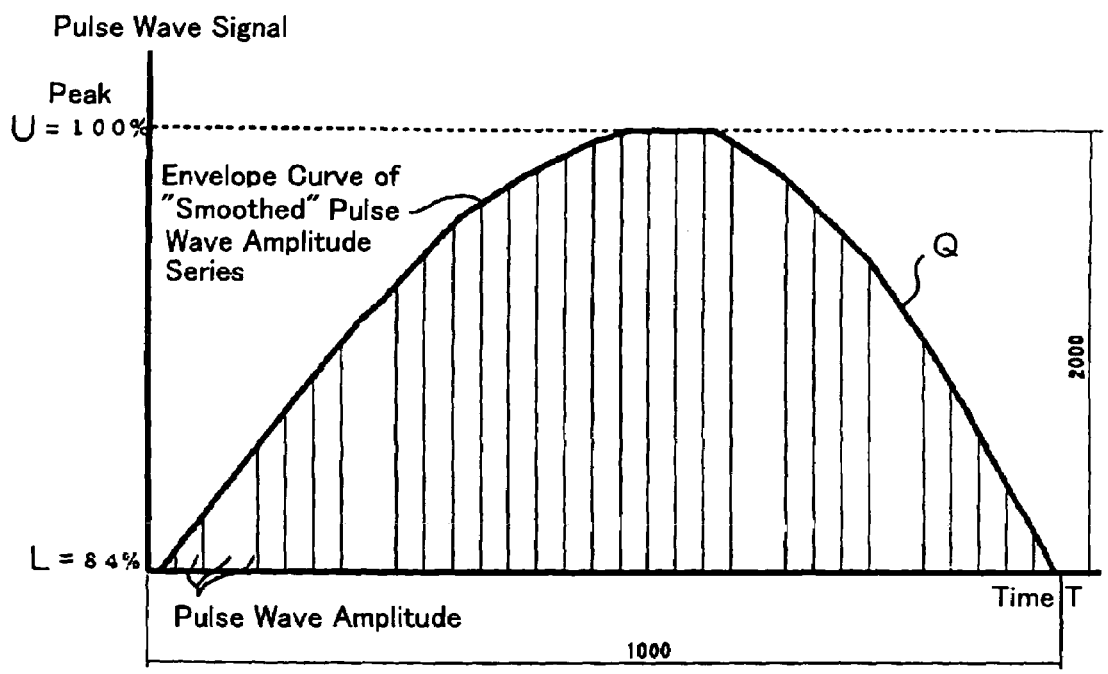
FIG. 6 shows a graph of pattern normalization in accordance with an embodiment of the present invention.

Next, as FIG. 6 indicates, normalization (standardization) is performed to determine the ranges of pattern portion Q on the horizontal X-axis and vertical Y-axis. In this normalization process, the ranges of pattern portion Q on the horizontal and vertical axis are set as predefined values, respectively. For instance, aforementioned pattern portion Q of pulse wave amplitude pattern P is normalized by setting its range on the x-axis, which indicates time, as 1000, and the range on the Y-axis, which indicates pulse wave amplitude, as 2000. Here, since the goal of this process is simply to normalize the size of the X-axis and Y-axis coordinates of pattern portion Q of the pulse wave amplitude pattern P, the sizes of the coordinates of the post-normalized X-axis (1000 in above example) and Y-axis (2000 in above example) ranges may be assume any value as long as they are constant.

[Pattern Area Matching Process (SST2)]

Figure 7:
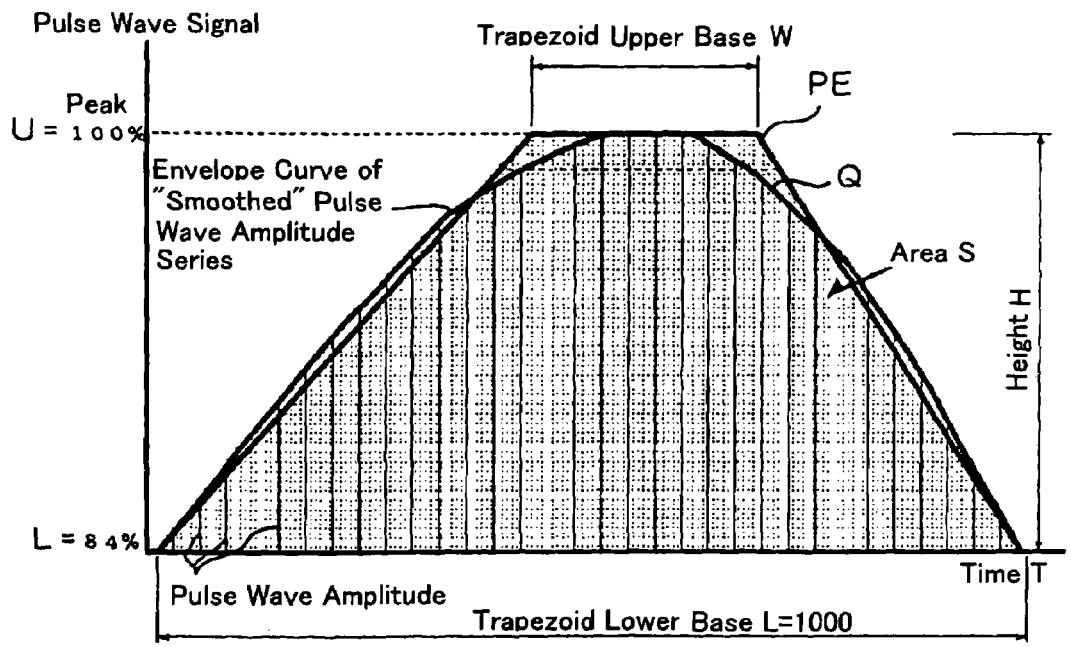
FIG. 7 shows a graph of pattern area matching process in accordance with an embodiment of the present invention.

Next, the pattern area of normalized pattern portion Q of the pulse wave amplitude pattern P is calculated. This pattern area is pursued by extending and integrating the envelope curve of pattern portion Q over the entirety of the values for X. When pattern area S of pattern portion Q is calculated in the aforementioned manner, as indicated in FIG. 7, general pattern PE which possesses the same area as pattern area S is established. In the case of the present embodiment, general pattern PE is limited in shape to a trapezoid but the size and shape of that trapezoid are not limited.

Since the aforementioned general pattern PE is a trapezoid, lower base width L, height H, and upper base width W may be assumed, and when set equal to a pattern area S, the following equation is established.

$$S=(L+W)\times H/2 \qquad (1)$$

Thus, if lower base width L of general pattern PE is the length of the bottom (in other words, the range on X-axis=1000) of aforementioned pattern portion Q and the height H of general pattern PE is the height (range on Y axis=2000) of aforementioned pattern portion Q, upper base width W may be calculated using aforementioned Equation 1. The elements of the fundamental shape of general pattern PE are decided in this manner.

[Pattern Shape Matching Process (SST3)]

Next, additional and more precise matching is performed with the shape of general pattern PE, the fundamental elements of which were derived according to the above method. Essentially, this process performs a superimposing operation to ensure that general pattern PE and pattern portion Q are in alignment (SST3).

Figure 8:
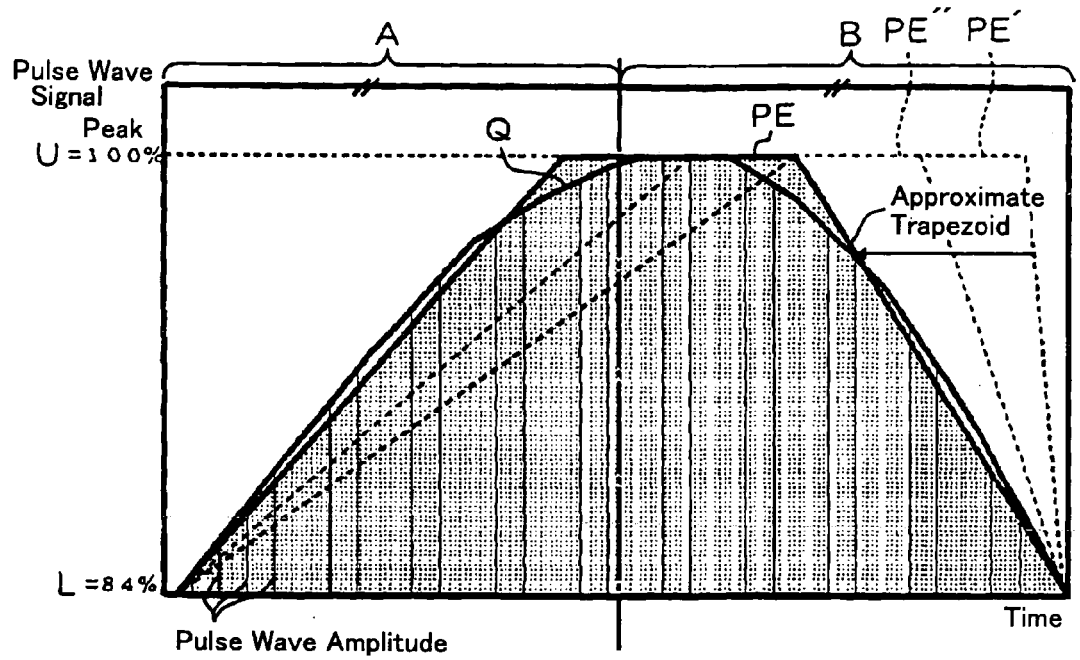
FIG. 8 shows a graph of pattern shape matching process in accordance with an embodiment of the present invention.

First, as FIG. 8 indicates, since lower limit L of aforementioned general pattern PE is equal to the length of the bottom of pattern portion Q on the X-axis, the XY coordinates are positioned so that the lower bases of general pattern PE and pattern portion Q are in conformity, at which time the range of the upper base (of general pattern PE) on the X-axis is adjusted to match to the maximum extent possible with the upper part of the aforementioned pattern portion Q. Various methods for this adjustment are conceivable, but in the present embodiment, a perpendicular line parallel to the Y-axis is assumed to pass through the center of lower base width L (the center of the range of general pattern PE over the x-axis). By splitting general pattern PE along this line, regions A and B are assumed, after which, the areas Z in regions A and B where general pattern PE (here, first general pattern PE is assumed) is not in alignment with aforementioned pattern portion Q are calculated. At this point, the upper base of the general pattern PE is shifted horizontally by a predefined amount δX (for instance ¼ of lower base width L of general pattern PE) in the direction of the side with the smallest amount of areas Z (region A in the figure), to obtain general pattern PE". Then, areas Z of the shifted general pattern PE" are re-calculated with the same aforementioned process and the upper base of general pattern PE" is shifted again in the direction of the side with the smallest area Z at half of predefined δX. This process is repeated, where the degree of conformity of general pattern PE and aforementioned pattern portion Q increases gradually with decrease in predefined amount δX/2n (where n is the number of times this process is performed), until the position of upper base position is obtained where the difference of the aforementioned areas Z of regions A and B are at their minimal amounts. Furthermore, the means for conducting this pattern shape matching process in control unit 10 composes the aforementioned pattern shape matching means. This process enables optimum setting of the initial shape of general pattern PE. For instance, the initial shape of the general pattern PE may be assumed to be the shape where the upper base is positioned over the central part of the lower base.

[Pattern Determination Process (SST4 to SST6)

Figure 9:
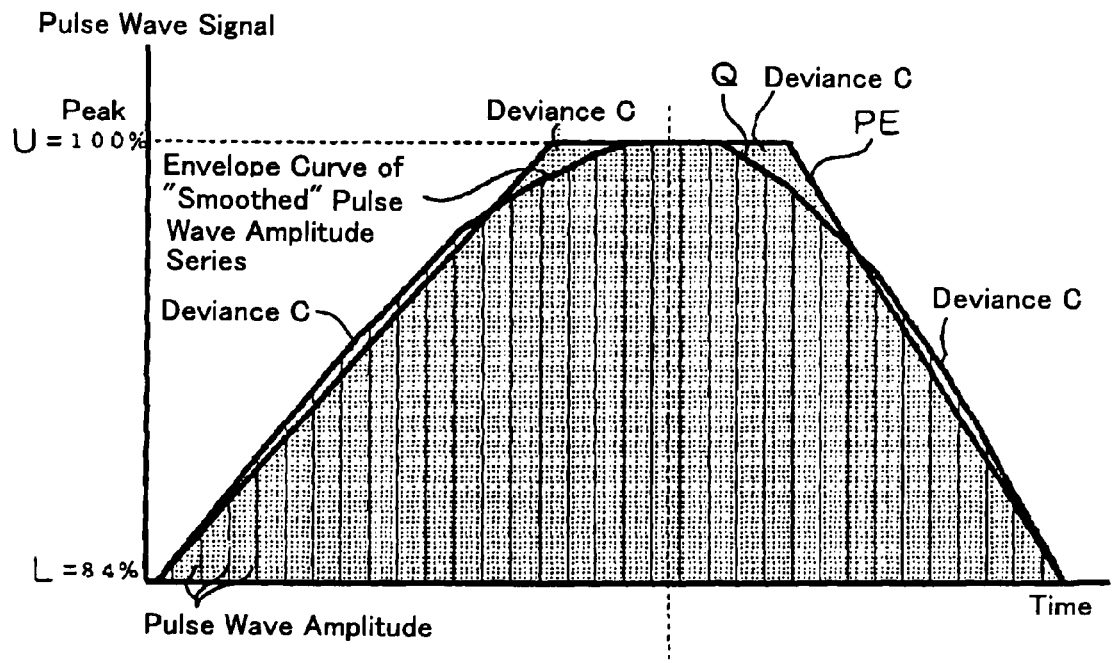
FIG. 9 shows a graph to explain precision index RA of pattern matched shape in accordance with an embodiment of the present invention.

Next, the matching shape of general pattern PE obtained from the aforementioned process is determined. This pattern determines to what extent overall general pattern PE conforms with aforementioned pattern portion Q of the pulse wave amplitude pattern. As FIG. 9 indicates, this process establishes total area V of regions C, regions where the matching shape of general pattern PE and aforementioned pattern portion Q of the pulse wave amplitude pattern are not in alignment. This total area V is the total of the area where general pattern PE exists but aforementioned pattern portion Q does not exist, and likewise, the area where aforementioned pattern portion Q exists but general pattern PE does not exist. Precision index RA is the value of total area V divided by pattern area S of aforementioned pattern portion Q. This precision index RA indicates the overall degree of conformity of matching of general pattern PE (matched by method described above) with aforementioned pattern portion Q. The matched shape of general pattern PE becomes closer to aforementioned pattern portion Q as precision index RA grows smaller. As a result, precision index RA establishes the degree to which the matched shape of general pattern PE conforms with pattern portion Q.

In the present embodiment, in the case that aforementioned precision index RA does not fall within the tolerance level (for instance value within range of 5 to 10%), in other words, the index exceeds a standard value, the determination is made that trapezoidal general pattern PE has not sufficiently expressed the profile of the shape of aforementioned pattern portion Q (SST4), and the process returns to aforementioned pattern identification process (SST1). At this time in the process of pattern identification, the value for the lower limit L is different from that of the previous round. In the case of the present embodiment, since lower limit L is initially set relatively high as 84% (hereinafter, simply designated as L=0.84) of the peak value of aforementioned pattern portion Q, the value is set lower than the initial round. For instance, if the degree of reduction of lower limit L is assumed to be 0.04, the calculation L=L−k is conducted yielding L=0.80. Using this new reduced lower limit L, the aforementioned pattern identification process (SST1) and the pattern shape matching Process (SST2) are repeated.

If precision index RA is outside the tolerance range, it is also acceptable to adjust upper limit U as an alternative to lowering lower limit L, and in other embodiments, even the range of aforementioned pattern portion Q may be varied. However, in the case of the present embodiment, adjusting lower limit L is most preferable, but there are cases when adjusting upper limit U also can yield results. It is also possible to adjust both lower limit L and upper limit U at the same time.

Figure 10:
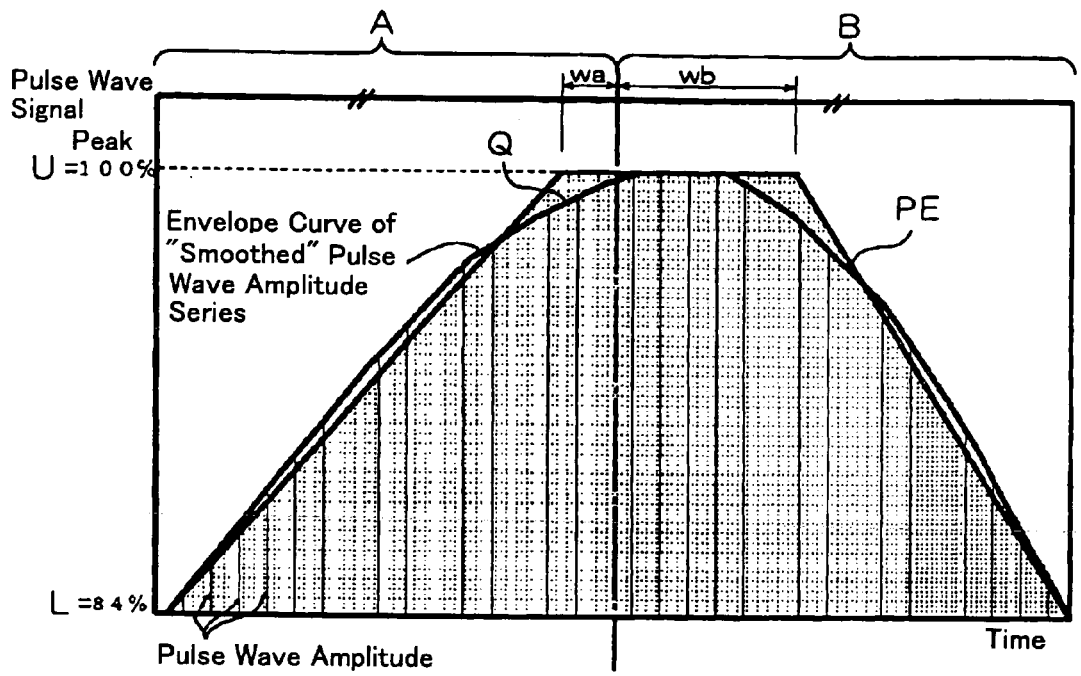
FIG. 10 shows a graph to explain precision index RB of pattern matched shape in accordance with an embodiment of the present invention.

When aforementioned precision index RA falls within the tolerance range, the next step is to determine the degree of distortion of the matching shape of general pattern PE by after-mentioned precision index RB (SST5). When general pattern PE is significantly distorted to the left or right, there is a strong possibility that the shape of aforementioned pattern portion Q has deviated from the original pulse wave amplitude pattern shape as a result of noise or some other reason. Thus, in the present embodiment, as indicated by FIG. 10, general pattern PE is split at the center of lower base width L. Once split, wa is assumed to be the width of the left range of upper base width W that belongs to range A and wb is assumed to be the width of the right range of upper base width W that belongs to range B. Precision index RB is then calculated as the ratio of wa and wb (RB=wa/wb). Then, RB is assessed as falling within a tolerance range (for instance, 0.8<RB<1.2), in other words, as whether wa and wb are close to being equal. Moreover, it is also acceptable to assess whether the difference of wa and wb (wa−wb) falls within a tolerance range (for instance, −0.2W<RB<0.2W) rather than using aforementioned ratio of wa/wb.

In the present embodiment, when aforementioned precision index RB falls outside of the tolerance range, the ranges of pattern portion Q (for instance, lower limit L) are adjusted in a manner similar to aforementioned SST4, and the pattern identification process (SST1) and pattern shape matching process (SST2) are repeated.

Figure 11:
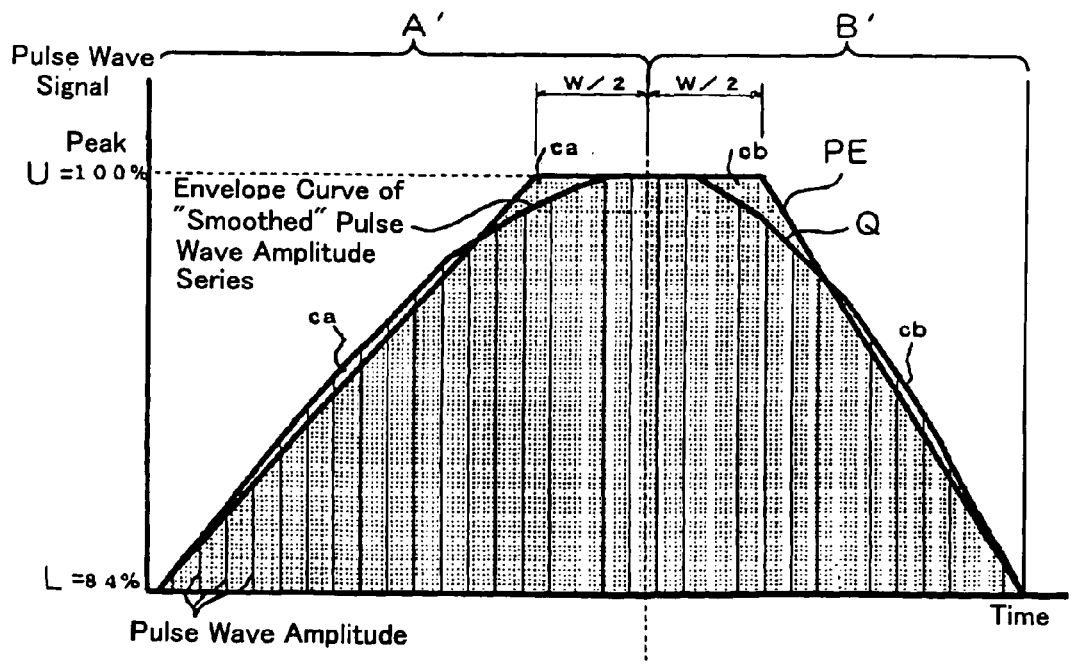
FIG. 11 shows a graph to explain precision index RC of pattern matched shape in accordance with an embodiment of the present invention.

When precision index RB is within the tolerance range, the next step is to determine whether the degree of conformity of the matching shape of general pattern PE is balanced on the left and right by after-mentioned precision index RC (SST6). Even if the matching shape of general pattern PE sufficiently reflects the shape of pattern portion Q overall, the matching shape of general pattern PE cannot be said to be practically reflecting the shape of aforementioned pattern portion Q if the degree of conformity is insufficiently balanced on the right and left. For this reason, in the present embodiment, as indicated in FIG. 11, regions A' and B' are created by dividing general pattern PE at the center of upper base width W. Areas in regions A' and B' where general pattern PE and aforementioned pattern portion Q are not in alignment (do not overlap) are designated as areas ca and cb, respectively. The difference between areas ca and areas cb is the precision index RC.

When precision index RC does not fall within a pre-designated tolerance range (for instance−(ca+cb)/5<RC=ca−cb<(ca+cb)/5), lower limit L is adjusted in a manner similar to SST4 and SST5 and pattern identification process (SST1) and pattern shape matching process (SST2) are repeated. At this time, lower limit L may be adjusted in a manner similar to that of SST4. Furthermore, aforementioned precision index RC may be assumed to be the ratio of aforementioned areas ca and cb.

Furthermore, while the present embodiment pursues each of precision indices RA, RB, and RC, it is also acceptable to determine only one of any three of these precision indices.

In addition, if at least one of the three precision indices does not fall within the tolerance range after repeating the aforementioned process; for instance, when the process has been repeated a specified number of times but the precision index still does not fall within the tolerance range, it is preferable that operation proceeds to the next process, where in addition to derivation of the cardiovascular dynamics index that is conducted with normal process, there is a display of the precision index or the fact that the accuracy of the cardiovascular dynamics index is low. The means for conducting the above processes and their contents in control unit 10 comprise the pattern determination means.

[Process of Derivation of Cardiovascular Dynamics Index (SST7)]

Figure 29:
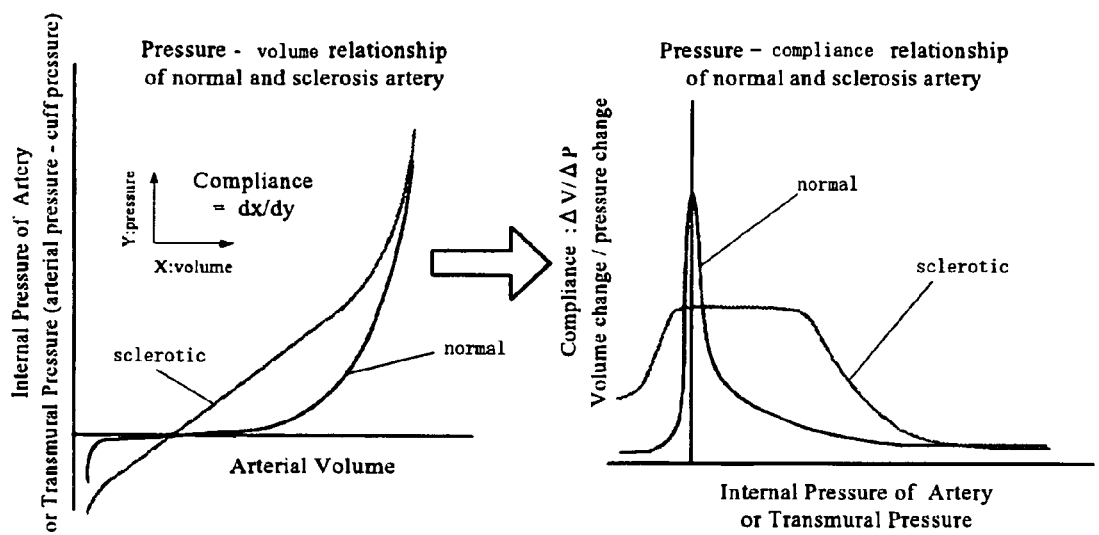
FIG. 29 shows a graph to explain pressure-volume relationship of normal and sclerotic artery.

Since general pattern PE that was matched in the manner described above may be judged to sufficiently reflect the shape of aforementioned pattern portion Q when the aforementioned precision indices RA, RB, and RC are within the aforementioned tolerance ranges, the cardiovascular dynamics index may be derived (SST7) based on the shape of the matched general pattern PE. In this process, the cardiovascular dynamics index is derived from the trapezoidal matching shape of general pattern PE that reflects pattern portion Q of the pulse wave amplitude pattern P. Here, either the upper base width W of the matched shape of general pattern PE or a pre-defined calculation based on this upper base width W may be employed as the cardiovascular dynamics index. Since upper base width W is the extracted characteristic of the shape of the area of maximum amplitudes in pulse wave amplitude pattern P, it may be considered to reflect the mechanical characteristics of the artery, and in particular, the elasticity characteristic of the arterial intima $1a$ and tunica media $1b$. This may also be understood from the fact that when sclerosis occurs in the arterial intima $1a$ and tunica media $1b$ as indicated in FIG. 29, a change occurs in regions of small transmural pressure in the arterial pressure-volume characteristic, and arterial compliance exhibits notable decline. In this manner, when sclerosis occurs in the artery, the shape of the area of maximum pulse wave amplitudes of the pulse wave amplitude pattern P changes, and it is usually the case that the area of maximum pulse wave amplitudes appears to be flat.

Figure 12:
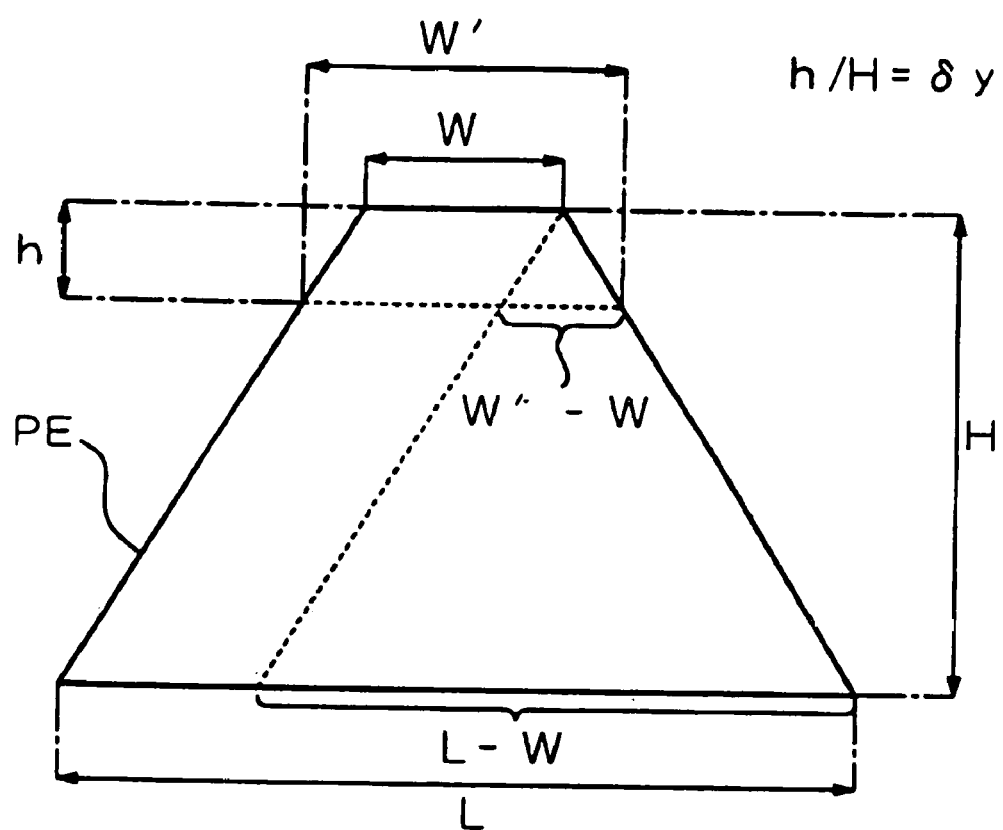
FIG. 12 shows a graph to explain process of deriving Range W' in accordance with an embodiment of the present invention.

However, in the present embodiment, it can be expected, depending on pulse wave amplitude pattern P, that general pattern PE will in some cases form a triangular shape (in other words, upper base width W is 0). As indicated in FIG. 12, these cases can be avoided, and the influence of noise minimized, by determining W', the width of general pattern PE at a specified height δy below upper base width W. Here δy is a height that is a specified proportion of height H of general pattern PE. For instance, when assuming the height of general pattern PE to be 100%, W' can be the width of general pattern PE where the height has been lowered 5% (in other words y is a position at 95% of the height). This width W' is derived with the equation (2) below.

$$W'=W+(L-W)\cdot h/H=W+(L-W)\delta y \quad (2)$$

Here, h is the distance from the upper base to W', and δy=h/H. δy may be adjusted for an optimal value, but in the case of the present embodiment, it is preferable to maintain δy within a range of 0.01 to 0.10 (1 to 10%). If δy is too small, the meaning of its use is lost, and if it is too large, information concerning upper base width W of general pattern P becomes difficult to integrate into the cardiovascular dynamics index, and an index that reflects the elastic characteristics of the arterial intima $1a$ and tunica media $1b$ may become unobtainable.

Figure 13:
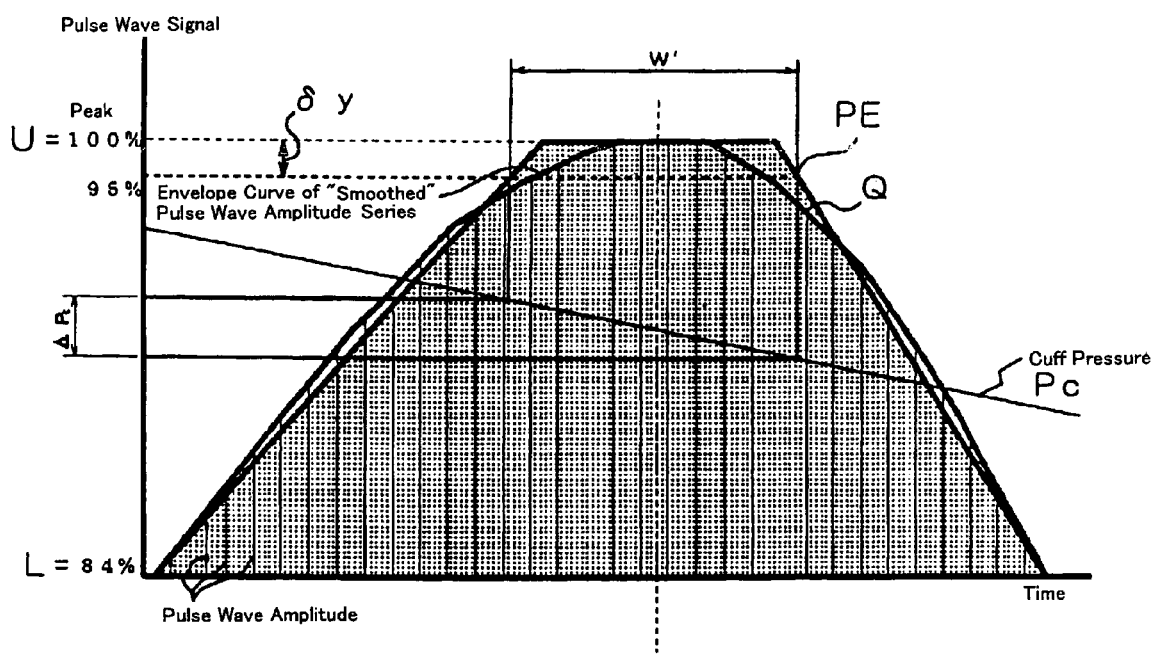
FIG. 13 shows a graph to explain process of deriving cardiovascular dynamics index RX in accordance with an embodiment of the present invention.

As FIG. 13 indicates, the present embodiment pursues pressure difference ΔPc of cuff pressure Pc corresponding with the width W' determined in the manner described above. The reason that pressure difference ΔPc of cuff pressure Pc corresponding with the width W' can be pursued is that an index independent of release rate and other measurement conditions can be achieved by converting the width W' into pressure difference ΔPc, since cuff pressure Pc is the external pressure value during pulse wave measurement. In other words, though conditions at the time of measurement may affect the amplitudes and time range of the pulse wave amplitude pattern P, which will in turn affect the width W', the objectivity of the cardiovascular dynamics index ASI can be raised since the influence of measurement conditions is minimized by deriving the cardiovascular dynamics index ASI from the pressure differential ΔPc. The cardiovascular dynamics index ASI (Arterial Stiffness Index) may be calculated as ΔPc (obtained in the way described above) itself or as a constant multiple of ΔPc (for example, a number in the range of 2 to 100). Here ASI is a trademark of the applicant of this present invention. The means for conducting the above processes in control unit 10 comprise the index derivation means for deriving the cardiovascular dynamics index.

Figure 14:
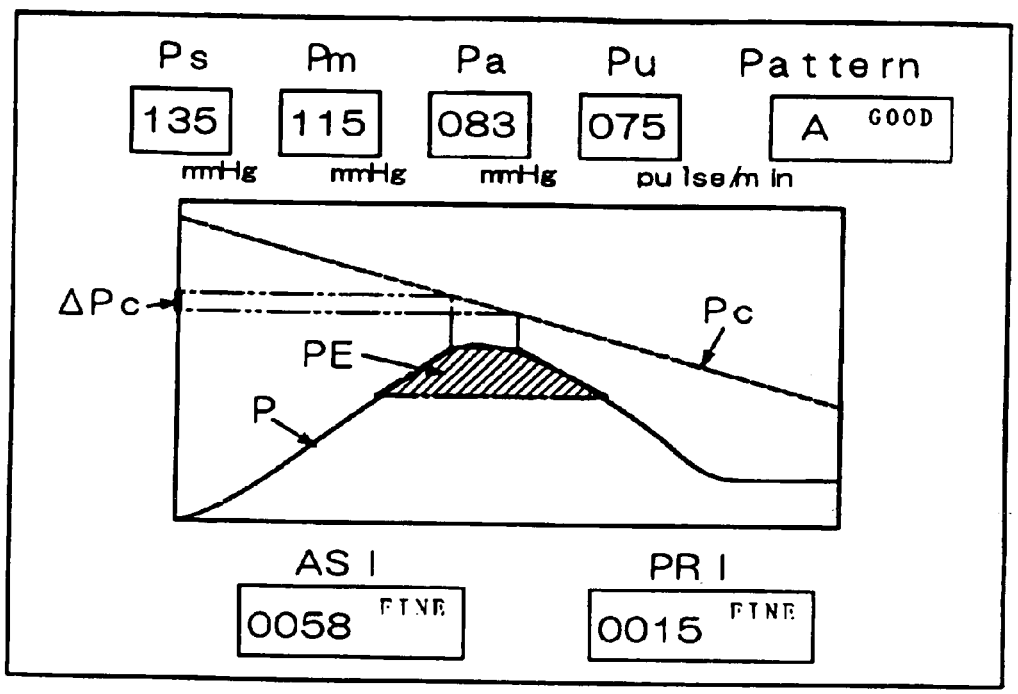
FIG. 14 shows a plain view of display screen of analysis results in accordance with an embodiment of the present invention.

The matching shape of general pattern PE, the aforementioned precision indices RA, RB, RC, and the cardiovascular dynamics index ASI obtained by the processes described above are displayed by display apparatus 22, printed by printing apparatus 23, and/or output from input-output terminal posts 24. FIG. 14 indicates an example of a display screen of these results. Here, the cardiovascular dynamics index ASI of the present embodiment is based on the shape of the area of the peak of the pulse wave amplitude pattern P, and its result serves as an index that indicates the arterial elastic characteristic, in other words, the elasticity of the intima $1a$ and tunica media $1b$. Here, in the present embodiment, ASI=ΔPc×10.

In addition, a total precision index PRI, derived from some addition, average, or multiple of precision indices RA, RB, and RC, is displayed in the top of the aforementioned screen indicated in FIG. 14. Total precision index PRI indicates the degree of compliance between the matching shape of general pattern PE and the pulse wave amplitude pattern. Here, PRI=a×RA+b×RB+c×RC, where a, b, and c are each respectively a pre-defined coefficient. However, it is also possible to derive total precision index PRI from one or two of precision indices RA, RB, and RC, and its derivation is not necessarily limited to the method described above.

Here, display apparatus 22 displays the superimposition of general pattern PE and pulse wave amplitude pattern P (or pattern portion Q) on screen as indicated in FIG. 14. Since the degree to which pulse wave amplitude pattern P or pattern portion Q matches general pattern PE can be visually established from this superimposed display, the validity of the cardiovascular dynamics index ASI derived on the basis of the general pattern PE pattern matching shape can also be established visually.

As indicated in FIG. 14, with the aforementioned input-output apparatus, it is possible to simultaneously display or output each blood pressure value (systolic blood pressure Ps, mean blood pressure Pm, diastolic blood pressure Pa) and pulse rate Pu, and furthermore, it is possible to conduct a classification means to determine one of the fundamental patterns listed in FIG. 23, the result of which may also be displayed or output.

The process of classification of pulse wave pattern P with Fundamental Patterns A through E indicated in FIG. 23 can be conducted with various pattern recognition methods (for instance, the method defined in Patent Document JP3470121B), but classification may also be accomplished by pattern area matching process, pattern shape matching process, and pattern determination process related to the present invention. For instance, the general patterns PE1 to PE3 displayed in FIG. 5 may be applied sequentially to pulse wave amplitude pattern P, an area identical to pulse wave amplitude pattern P may be established in the same manner as the aforementioned pattern area matching process, shape matching may be performed in the same manner as aforementioned pattern shape matching process, and precision indices RA, RB, RC and total precision index PRI may be derived in the same manner as aforementioned pattern determination process to determine the degree of conformity indicating which of these general patterns PE1 to PE3 is most appropriate. When general pattern PE1 is determined to be the most appropriate, further classification into Fundamental Pattern A or B is conducted according to the size of the absolute maximum value of the pulse wave amplitudes, and when general pattern PE2 is determined to be most appropriate, it is classified as Fundamental Pattern C, and in the case that general pattern PE3 is judged to be most appropriate, it is classified as Fundamental Pattern E. When no appropriate general pattern can be determined for pulse wave amplitude pattern P (the case when aforementioned precision indices or total precision index diverges from tolerance range), it is classified as Fundamental Pattern D.

In the present embodiment, after matching a general pattern PE with pattern portion Q of pulse wave amplitude pattern P, the cardiovascular dynamics index ASI is derived from the shape of the matched general pattern PE. However, even if the matching shape of general pattern PE is not expressed by processing, or it is not displayed in the processing results, it is possible to calculate the cardiovascular dynamics index ASI by performing what is in essence the same calculation process as above, and this aspect also is included in the range of the present invention.

The present embodiment expresses pattern portion Q that is at least a portion of pulse wave amplitude pattern P as a pre-established general pattern PE matched shape and determines the cardiovascular dynamics index ASI based on this general pattern PE matched shape. Establishment of the overall pattern shape, the process that matches general pattern PE, and the determination of an accurate and clear cardiovascular dynamics index ASI are all easily accomplished by making the area of general pattern PE matched shape equal to the area of at least a portion of pulse wave amplitude pattern P. In other words, because overall compliance between pattern portion Q and general pattern PE can be secured by establishing the area of pattern portion Q of pulse wave amplitude pattern P as equal to the area of general pattern PE matched with pattern portion Q, the degree of accuracy of cardiovascular dynamics index ASI can be further increased. In addition, by making the area of pattern portion Q and general pattern PE equal, the matching parameters for conducting the matching process are decreased in number and the matching process can be conducted with greater ease.

In addition, since the present embodiment can establish the degree of accuracy of the matched shape of general pattern PE by employing the areas where the matched shape of general pattern PE and pulse wave amplitude pattern P (pattern portion Q) are not in alignment to determine the precision indices RA, RB, and RC or the total precision index PRI of the matched shape of general pattern PE, it is also possible to establish the reliability of the cardiovascular dynamics index.

Furthermore, since the display apparatus displays 22 the superimposition of the matched shape of the general pattern PE and the pulse wave amplitude pattern P (pattern portion Q), it is possible establish the reliability of the cardiovascular dynamics index from the ability to visually assess the state of pattern matching.

In addition, in the present embodiment, general pattern PE is a trapezoid where the lower base width L is the width of the bottom of pattern portion Q of pulse wave amplitude pattern P and height H is the maximum value of pattern portion Q of pulse wave amplitude pattern P. Since the trapezoidal general pattern PE is easily and unambiguously established in this manner, upper base width W can be easily obtained by establishing the area of the trapezoidal general pattern PE as equal to pattern portion Q of the pulse wave amplitude pattern P.

In the present embodiment, cardiovascular dynamics index ASI is derived based on an adjustable threshold set at a prescribed position below the upper base of general pattern PE. In this manner, the effect of the noise present in the area of the peak of pulse wave amplitude pattern P can be reduced by basing derivation of the cardiovascular dynamics index ASI on a range positioned at a height of a predefined percentage below the position of the top of the upper base rather than on the range of the upper base itself. In addition, the upper base width W of the general pattern PE can be extremely small (in some cases 0) depending upon the shape of the peak of the pulse wave amplitude pattern P, in which case the reliability of the cardiovascular dynamics index ASI can be expected to significantly decrease, but stability of the cardiovascular dynamics index ASI can be achieved through the method described above, which consequently strengthens reliability as well.

Figure 15:
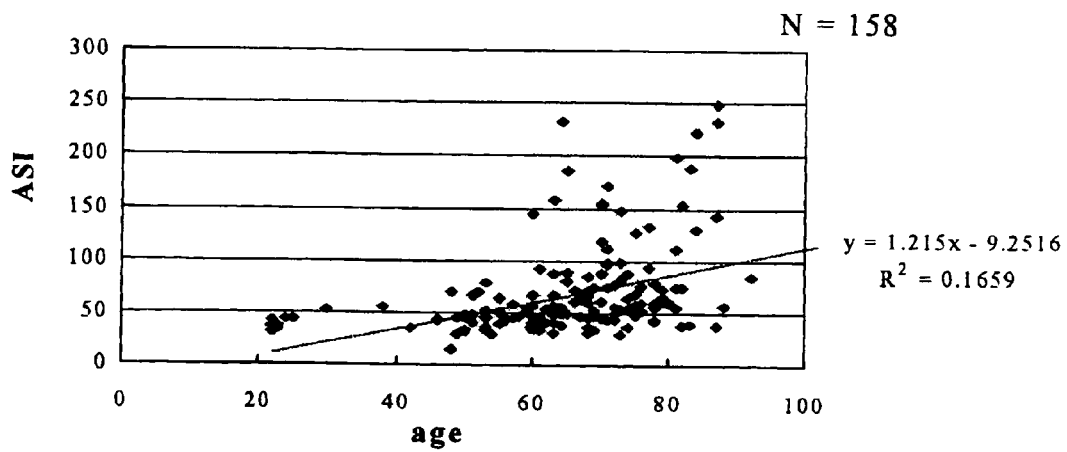
FIG. 15 shows a graph to explain relationship of ASI and age.

FIG. 15 displays the degree of dependence of aforementioned cardiovascular dynamics index ASI on age when measurement was performed on 158 outpatients. It was not possible to absolutely determine cardiovascular state on the basis of blood pressure alone as many of the outpatients were taking anti-hypertensive medication, but correlation was clearly admitted with cardiovascular dynamics index ASI and age, and in addition, the range of cardiovascular dynamics index ASI was shown to increase with age.

Furthermore, when comparison of fore and rear data in the pulse wave amplitudes revealed the presence of an aberrant amplitude in the pulse wave amplitudes series acquired by the aforementioned embodiment, smoothing process ST11 was conducted using either of the following two methods: (1) exchanging process of data that exchanges the amplitude with the average of its fore and rear data to eliminate this aberrant amplitude: or (2) migration averaging process by migration averaging of the pulse wave amplitude series. However, smoothing process of the pulse wave amplitude series can also be conducted by reordering of the pulse wave amplitude series data. The smoothing process conducted by reordering this data is explained below with FIG. 16.

Figure 16:
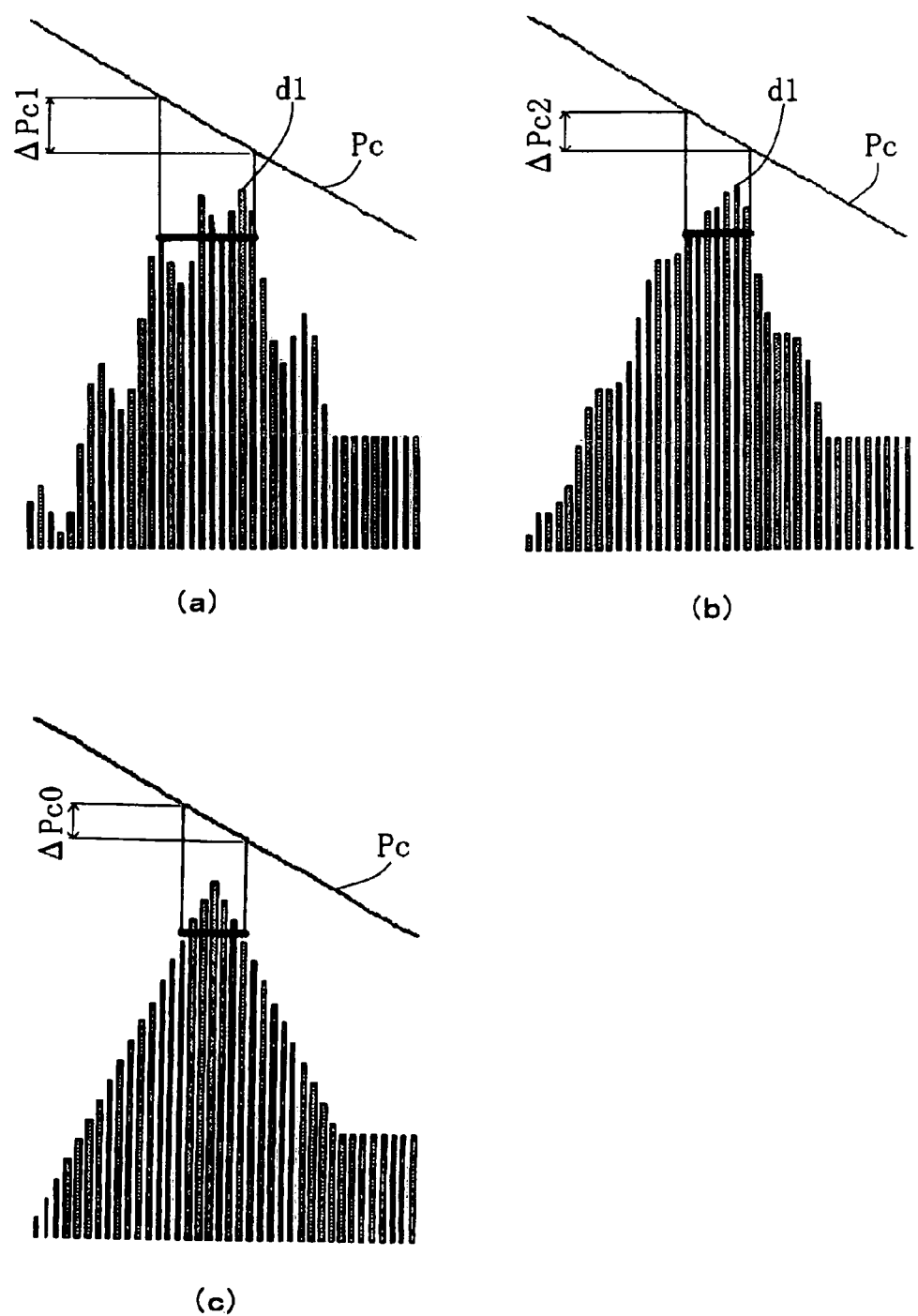
FIG. 16 shows several graphs of pulse wave amplitude series where a) shows a graph of a pulse wave amplitude data series derived during blood pressure measurement with fluctuation in blood pressure form respiration or body movement of the measurement subject, b) shows a graph of a pulse wave amplitude series that was acquired under the same conditions of fluctuation in blood pressure but the data has subsequently undergone reordering, and c) shows a graph of an ideal pulse wave amplitude series derived during blood pressure measurement without occurrence of blood pressure fluctuation from the breathing or body movement of the measurement subject and without the presence of noise.
Figure 17:
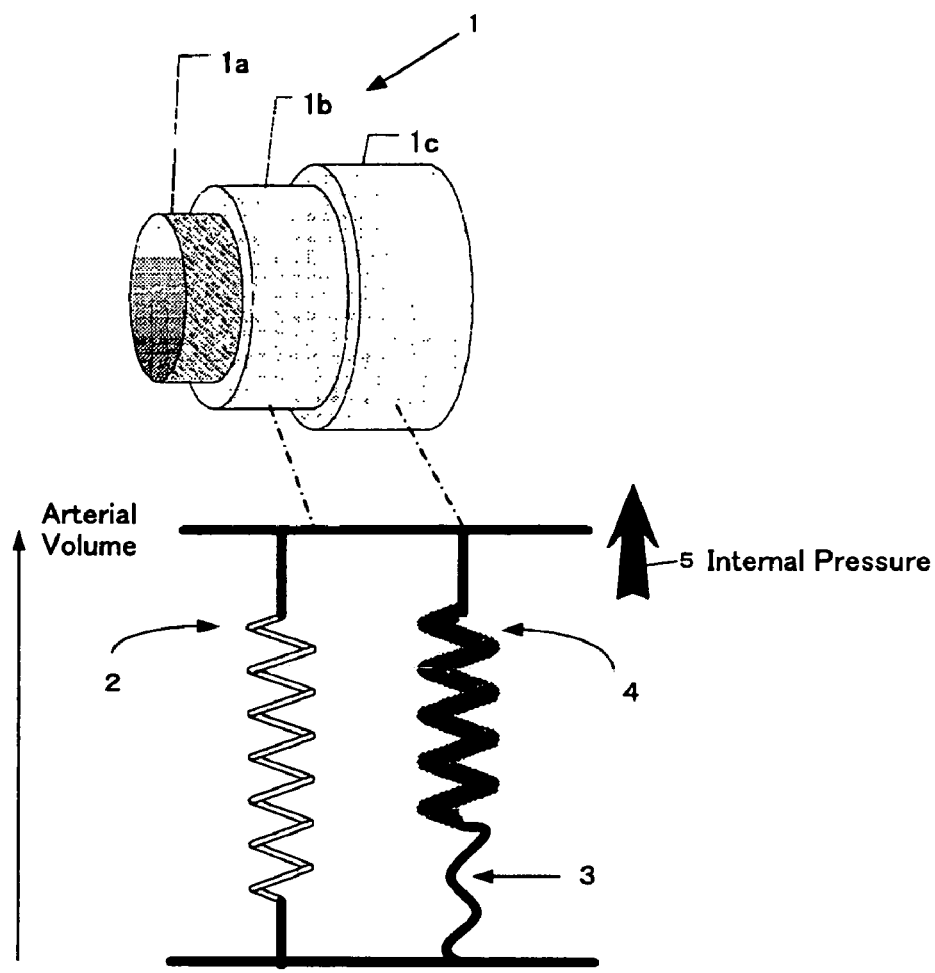
FIG. 17 shows a diagram to explain structure of the artery.
Figure 18:
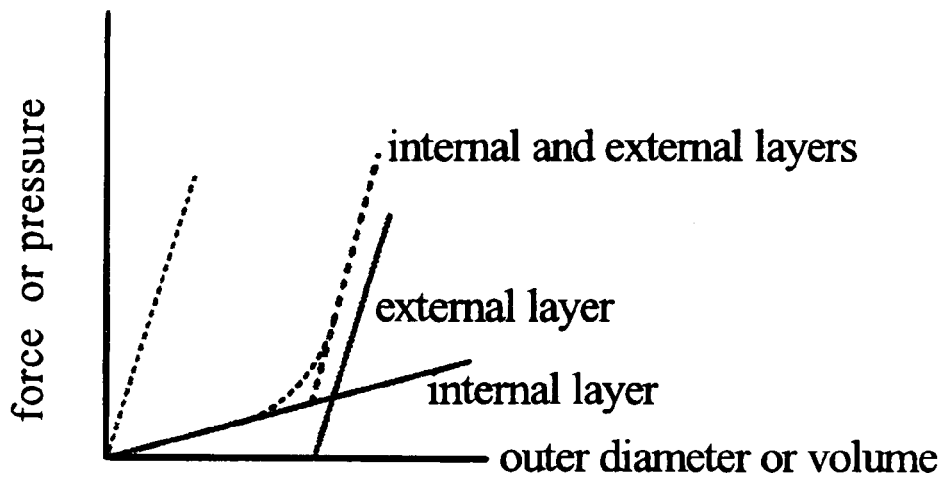
FIG. 18 shows a graph to explain relationship of arterial internal pressure and arterial volume.
Figure 19:
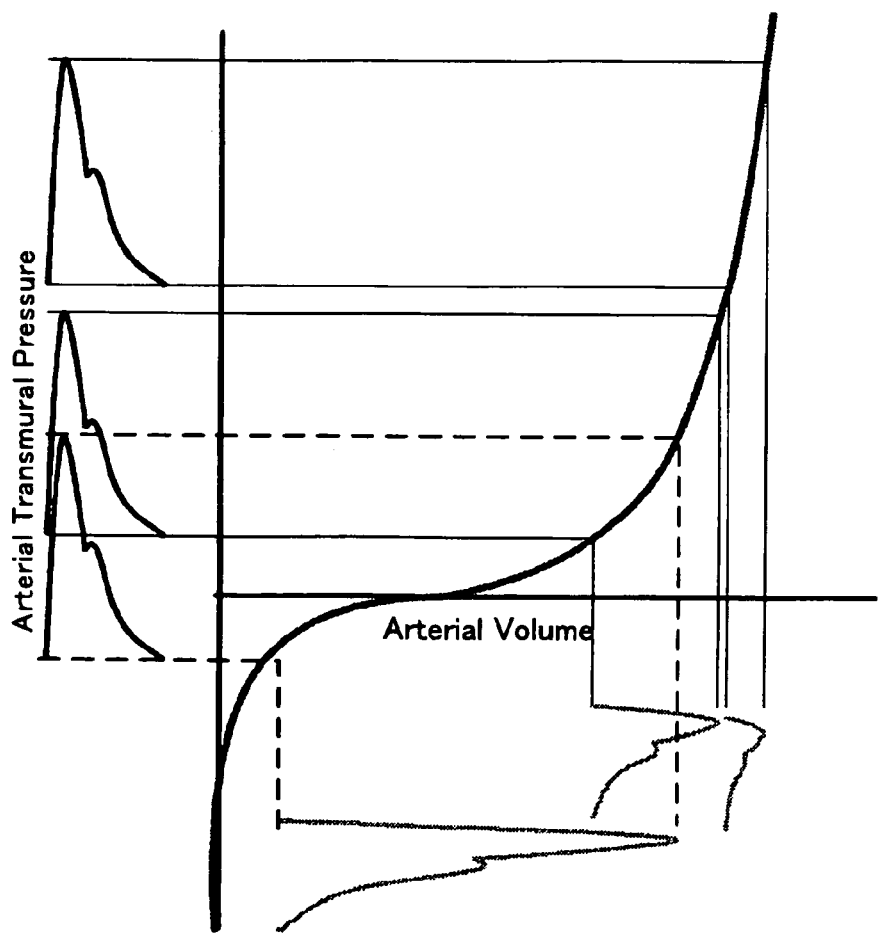
FIG. 19 shows a graph to explain relationship of transmural pressure and arterial volume.
Figure 20:
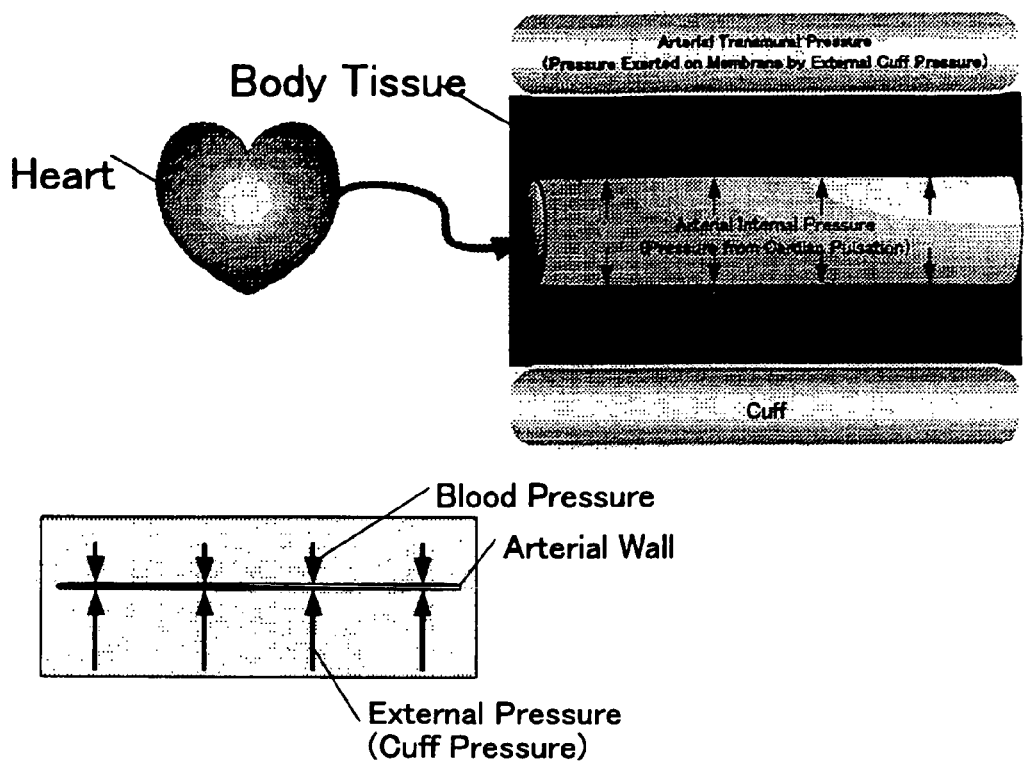
FIG. 20 shows a diagram to explain relationship of cuff pressure and arterial transmural pressure.
Figure 21:
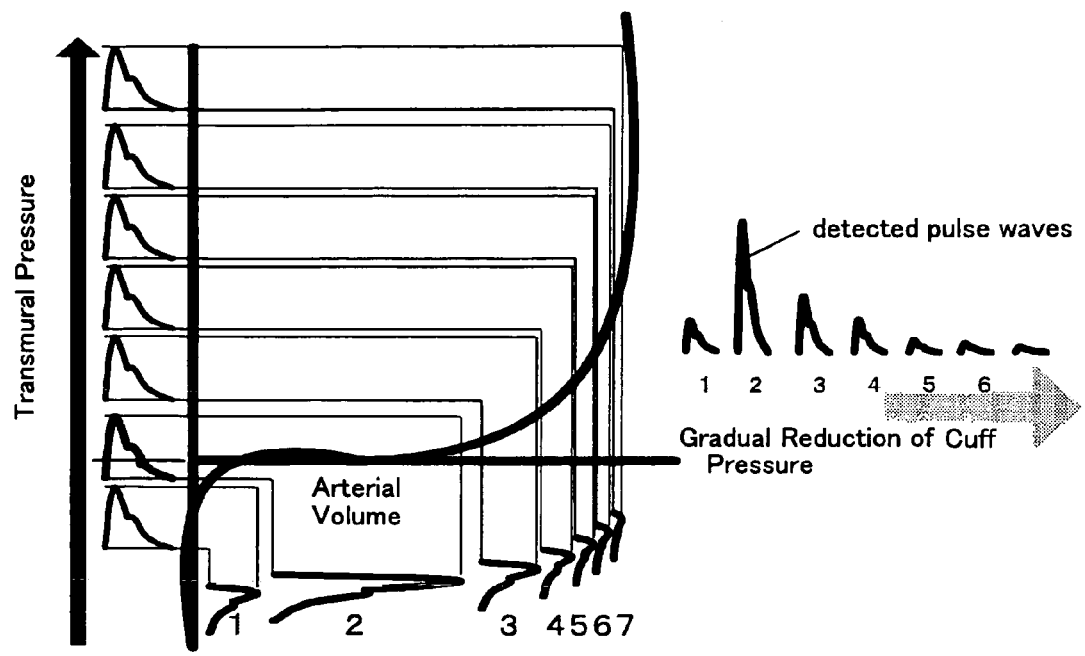
FIG. 21 shows a graph to explain variation in pulse wave shape due to relationship of arterial transmural pressure arterial volume.
Figure 22:
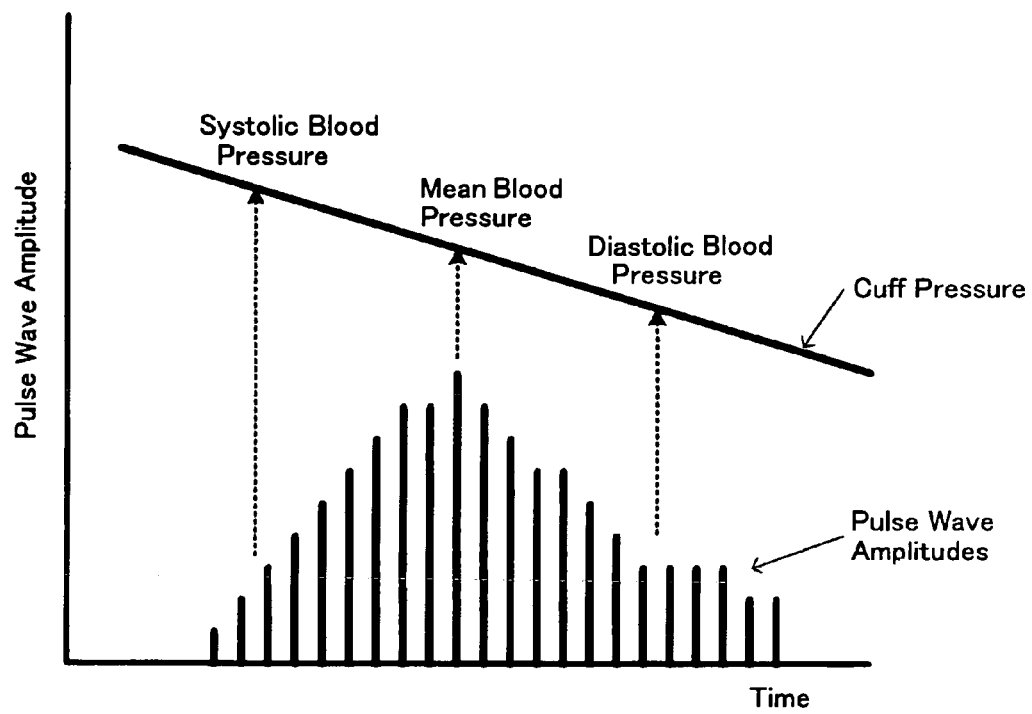
FIG. 22 shows a graph to explain relationship of pulse wave amplitude pattern and blood pressure values.

FIG. 16 indicates several graphs of pulse wave amplitude series where a) indicates a graph of a pulse wave amplitude data series derived during blood pressure measurement where fluctuation in blood pressure from respiration or body movement of the measurement subject has occurred, b) indicates a graph of a pulse wave amplitude series that was acquired under the same conditions of fluctuation in blood pressure but the data has subsequently undergone reordering, and c) indicates a graph of an ideal pulse wave amplitude series derived during blood pressure measurement without occurrence of blood pressure fluctuation from the breathing or body movement of the measurement subject and without the presence of noise.

Because as FIG. 16(a) indicates a pulse wave amplitude series derived during blood pressure measurement with fluctuation in blood pressure from respiration or body movement of the measurement subject does not assume a shape such as that in FIG. 6, where there is a maximum peak value that serves as a divider with amplitudes gradually rising until they reach this peak and then gradually declining after the peak, an error occurs in the calculation of the cardiovascular dynamics index ASI. The influence of blood pressure fluctuation from respiration or body movement of measurement subject may be suppressed and a highly accurate cardiovascular dynamics index may be obtained by conducting smoothing process that reorders that pulse wave amplitude data on the pulse wave amplitude series data indicated in FIG. 16(a) to produce the pulse wave amplitude series indicated in FIG. 16(b).

As FIG. 16(b) indicates, reordering of the pulse wave amplitude data is performed by splitting the pulse wave amplitude series data into two parts at the maximum peak value d1 and then reordering the pulse wave amplitude data to the left of maximum peak value d1 so that their values increase consecutively to maximum peak d1 and recording the pulse wave amplitude data to the right of maximum peak value d1 so that their values consecutively become smaller after maximum peak value d1.

When pulse wave amplitude pattern formulation and pressure difference ΔPc are pursued (as described above) following the reordering of the pulse wave amplitude data, the calculated pressure difference ΔPc2 is much closer to pressure difference ΔPc0, derived on the basis of the ideal pulse wave amplitude pattern, in comparison with pressure difference ΔPc1 derived from the pulse wave amplitude series where reordering data has not been performed, as is clear in FIG. 16. In other words, when the pulse wave amplitude pattern is formulated after the pulse wave amplitude data has been reordered, the influence of fluctuation in blood pressure from respiration or body movement of the measurement subject can be suppressed and a highly accurate cardiovascular dynamics index ASI can be achieved. In addition, since the influence of blood pressure fluctuation from respiration or body movement of the measurement subject can be suppressed, a highly stable blood pressure measurement value can be obtained. In FIG. 16, the envelope curve, general pattern PE, and other components necessary for calculation of the cardiovascular dynamics index ASI are not posted for reasons of abbreviation.

In addition, the exchanging data process described above is preferable to the migration averaging process as a method of smoothing process, and by performing the exchanging data process, it is possible to obtain a pulse wave series such as that indicated in FIG. 16(b). In other words, it is possible to obtain a more accurate cardiovascular dynamics index ASI by performing smoothing process with the exchanging data process rather than with the migration averaging process. Moreover, the procedure for reordering of data does not necessarily have to be simple reordering of data according to the size of data values as above but also may employ reordering of only those amplitudes where adjacent amplitudes exceed a constant value, reordering where time is used as a value, and other reordering procedures. In addition, both reordering of data and exchanging data process may be employed as a method of smoothing process.

As explained above, the present invention, by matching a polyangular general pattern with at least one pattern portion of the formulated pulse wave amplitude pattern, can reduce the influence of noise. In addition, the present invention offers the significant advantage of deriving a highly precise cardiovascular dynamics index that objectively indicates in particular the arterial mechanical properties.

What is claimed is:

1. Cardiovascular dynamics evaluation apparatus comprising:
   a pulse wave detection means for detecting pulse waves when external pressure is applied to the artery;
   a pulse wave amplitude pattern formulation means for formulating a pulse wave amplitude pattern that indicates the dependency characteristic of the pulse wave amplitude in regard to said external pressure from the value detected by said pulse wave detection means;
   a pattern shape matching means for matching general polyangular patterns to a pattern portion of said pulse wave amplitude pattern that includes at least a part of the envelope curve; and
   an index derivation means for deriving a cardiovascular dynamics index related to arterial mechanical characteristics and/or cardiac function, based on said general pattern matched shape;
   wherein the area of said general polyangular patterns is equal to the area of said pattern portion.

2. Cardiovascular dynamics evaluation apparatus according to claim 1, further comprising a pattern determination means for deriving said general pattern matched shape or a precision index of said cardiovascular dynamics index based on areas where said pattern portion and said general pattern matched shape do not overlap.

3. Cardiovascular dynamics evaluation apparatus according to claim 2, wherein said pattern shape matching means re-establishes said general pattern matched shape after adjusting range of said pattern portion when said precision index derived with said pattern shape matching means departs from a tolerance range.

4. Cardiovascular dynamics evaluation apparatus according to claim 1, comprising a further pattern display means for displaying the superimposition of at least said pattern portion of said pulse wave amplitude pattern and said general pattern matched shape.

5. Cardiovascular dynamics evaluation apparatus according to claim 1, wherein said pulse wave amplitude pattern formulation means formulates said pulse wave amplitude pattern after reordering data, using a prescribed procedure, in the pulse wave amplitude series derived on the basis of the values detected by said pulse wave detection means.

6. Cardiovascular dynamics evaluation apparatus comprising:
   a pulse wave detection means for detecting pulse waves when external pressure is applied to the artery;
   a pulse wave amplitude pattern formulation means for formulating a pulse wave amplitude pattern that indicates the dependency characteristic of the pulse wave amplitude in regard to said external pressure from the value detected by said pulse wave detection means;
   a pattern shape matching means for matching general trapezoid patterns to a pattern portion of said pulse wave amplitude pattern, that includes the envelope curve, that is defined by applying a lower limit threshold to said pulse wave amplitude pattern; and
   an index derivation means for deriving a cardiovascular dynamics index related to arterial mechanical characteristics based on said general pattern matched shape.

7. Cardiovascular dynamics evaluation apparatus according to claim 6, wherein the area of said general trapezoid patterns is equal to the area of said pattern portion.

8. Cardiovascular dynamics evaluation apparatus according to claim 7, wherein said index derivation means derives said cardiovascular dynamics index based on width of upper base of said general pattern matched shape.

9. Cardiovascular dynamics evaluation apparatus according to claim 7, wherein said index derivation means derives said cardiovascular dynamics index based on an adjustable threshold set at a prescribed position below the upper base of said general trapezoid patterns.

10. Cardiovascular dynamics evaluation apparatus according to claim 7, further comprising a pattern determination means for deriving said general pattern matched shape or a precision index of said cardiovascular dynamics index based on areas where said pattern portion and said general pattern matched shape do not overlap.

11. Cardiovascular dynamics evaluation apparatus according to claim 10, wherein said pattern shape matching means re-establishes said general pattern matched shape after adjusting range of said pattern portion when said precision index derived with said pattern shape matching means departs from a tolerance range.

12. Cardiovascular dynamics evaluation apparatus according to claim 7, comprising a further pattern display means for displaying the superimposition of at least said pattern portion of said pulse wave amplitude pattern and said general pattern matched shape.

13. Cardiovascular dynamics evaluation apparatus according to claim 7, wherein said pulse wave amplitude pattern formulation means formulates said pulse wave amplitude pattern after reordering data, using a prescribed procedure, in the pulse wave amplitude series derived on the basis of the values detected by said pulse wave detection means.

14. Cardiovascular dynamics evaluation apparatus according to claim 6, wherein said index derivation means derives said cardiovascular dynamics index based on width of upper base of said general pattern matched shape.

15. Cardiovascular dynamics evaluation apparatus according to claim 6, wherein said index derivation means derives said cardiovascular dynamics index based on an adjustable threshold set at a prescribed position below the upper base of said general trapezoid patterns.

16. Cardiovascular dynamics evaluation apparatus according to claim 6, further comprising a pattern determination means for deriving said general pattern matched shape or a precision index of said cardiovascular dynamics index based on areas where said pattern portion and said general pattern matched shape do not overlap.

17. Cardiovascular dynamics evaluation apparatus according to claim 16, wherein said pattern shape matching means re-establishes said general pattern matched shape after adjusting range of said pattern portion when said precision index derived with said pattern shape matching means departs from a tolerance range.

18. Cardiovascular dynamics evaluation apparatus according to claim 6, comprising a further pattern display means for displaying the superimposition of at least said pattern portion of said pulse wave amplitude pattern and said general pattern matched shape.

19. Cardiovascular dynamics evaluation apparatus according to claim 6, wherein said pulse wave amplitude pattern formulation means formulates said pulse wave amplitude pattern after reordering data, using a prescribed procedure, in the pulse wave amplitude series derived on the basis of the values detected by said pulse wave detection means.

20. Cardiovascular dynamics evaluation apparatus comprising:
   a pulse wave detection means for detecting pulse waves when external pressure is applied to the artery;
   a pulse wave amplitude pattern formulation means for formulating a pulse wave amplitude pattern that indicates the dependency characteristic of the pulse wave amplitude in regard to said external pressure from the value detected by said pulse wave detection means;
   a pattern shape matching means for matching general polyangular patterns to a pattern portion of said pulse wave amplitude pattern that includes at least a part of the envelope curve;
   an index derivation means for deriving a cardiovascular dynamics index related to arterial mechanical characteristics and/or cardiac function, based on said general pattern matched shape; and
   a pattern determination means for deriving said general pattern matched shape or a precision index of said cardiovascular dynamics index based on areas where said pattern portion and said general pattern matched shape do not overlap
   wherein said pattern shape matching means re-establishes said general pattern matched shape after adjusting range of said pattern portion when said precision index derived with said pattern shape matching means departs from a tolerance range.

21. Cardiovascular dynamics evaluation apparatus comprising:
   a pulse wave detection means for detecting pulse waves when external pressure is applied to the artery;
   a pulse wave amplitude pattern formulation means for formulating a pulse wave amplitude pattern that indicates the dependency characteristic of the pulse wave amplitude in regard to said external pressure from the value detected by said pulse wave detection means;
   a pattern shape matching means for matching general polyangular patterns to a pattern portion of said pulse wave amplitude pattern that includes at least a part of the envelope curve;
   an index derivation means for deriving a cardiovascular dynamics index related to arterial mechanical characteristics and/or cardiac function, based on said general pattern matched shape; and
   a pattern display means for displaying the superimposition of at least said pattern portion of said pulse wave amplitude pattern and said general pattern matched shape.

22. Cardiovascular dynamics evaluation apparatus comprising:
   a pulse wave detection means for detecting pulse waves when external pressure is applied to the artery;
   a pulse wave amplitude pattern formulation means for formulating a pulse wave amplitude pattern that indicates the dependency characteristic of the pulse wave amplitude in regard to said external pressure from the value detected by said pulse wave detection means;
   a pattern shape matching means for matching general polyangular patterns to a pattern portion of said pulse wave amplitude pattern that includes at least a part of the envelope curve; and an index derivation means for deriving a cardiovascular dynamics index related to arterial mechanical characteristics and/or cardiac function, based on said general pattern matched shape;

wherein said pulse wave amplitude pattern formulation means formulates said pulse wave amplitude pattern after reordering data, using a prescribed procedure, in the pulse wave amplitude series derived on the basis of the values detected by said pulse wave detection means.

* * * * *